(12) United States Patent
Mei et al.

(10) Patent No.: US 12,344,856 B2
(45) Date of Patent: Jul. 1, 2025

(54) PREPARATION METHOD AND SYSTEM FOR RECOMBINANT ADENO-ASSOCIATED VIRUS, AND RECOMBINANT BACMID

(71) Applicant: Genevoyager (Wuhan) Co., Ltd., Hubei (CN)

(72) Inventors: Ting Mei, Hubei (CN); Xiaobin He, Hubei (CN); Xing Pan, Hubei (CN); Sheng Zhang, Hubei (CN); Gang Huang, Hubei (CN); Mengdie Wang, Hubei (CN); Yu Zuo, Hubei (CN); Liang Du, Hubei (CN)

(73) Assignee: Genevoyager (Wuhan) Co., Ltd., Hubei (CN)

( * ) Notice: Subject to any disclaimer, the term of this patent is extended or adjusted under 35 U.S.C. 154(b) by 322 days.

(21) Appl. No.: 17/792,713

(22) PCT Filed: Dec. 18, 2020

(86) PCT No.: PCT/CN2020/137461
§ 371 (c)(1),
(2) Date: Jul. 14, 2022

(87) PCT Pub. No.: WO2022/116285
PCT Pub. Date: Jun. 9, 2022

(65) Prior Publication Data
US 2023/0090178 A1  Mar. 23, 2023

(30) Foreign Application Priority Data

Dec. 3, 2020 (CN) .......................... 202011393359.1

(51) Int. Cl.
C12N 15/86 (2006.01)

(52) U.S. Cl.
CPC .... *C12N 15/86* (2013.01); *C12N 2710/14044* (2013.01); *C12N 2750/14122* (2013.01); *C12N 2750/14143* (2013.01); *C12N 2750/14152* (2013.01)

(58) Field of Classification Search
None
See application file for complete search history.

(56) References Cited

U.S. PATENT DOCUMENTS

| | | |
|---|---|---|
| 2003/0148506 A1 | 8/2003 | Kotin et al. |
| 2004/0197895 A1 | 10/2004 | Kotin et al. |
| 2018/0155740 A1 | 6/2018 | Wu et al. |
| 2020/0208175 A1 | 7/2020 | Wu et al. |

FOREIGN PATENT DOCUMENTS

| | | |
|---|---|---|
| CN | 103827306 | 5/2014 |
| CN | 106544325 | 3/2017 |
| CN | 09609552 | 4/2019 |
| WO | 0011149 | 3/2000 |
| WO | 2020133772 | 7/2020 |

OTHER PUBLICATIONS

Possee, R. et al., Biotech. Bioengin., 2008, vol. 101: pp. 1115-1122.*
BacMagic DNA kit literature, EMD chemicals, 2009, 10 pages.*
Genbank entry KF022001, 2013, 60 pages.*
Yang Wu et al., "Popularizing recombinant baculovirus-derived OneBac system for scaling-up production of all recombinant adeno-associated virus vector serotypes", bioRxiv, Nov. 1, 2020, pp. 1-33.
Yang Wu et al., "A Recombinant Baculovirus Efficiently Generates Recombinant Adeno-Associated Virus Vectors in Cultured Insect Cells and Larvae", Molecular Therapy Methods & Clinical Development, Sep. 21, 2018, pp. 38-47.
M. Leticia Ferrelli et al., "The Baculoviral Genome", Viral Genomes—Molecular Structure, Diversity, Gene Expression Mechanisms and Host-Virus Interactions, Feb. 24, 2012, pp. 3-32.
Rohrmann Gf., "12. The AcMNPV genome: Gene content, conservation, and function", Baculovirus Molecular Biology [Internet], 4th edition, Jul. 22, 2019, pp. 2-75.
"International Search Report (Form PCT/ISA/210) of PCT/CN/2020/137461", mailed on Sep. 10, 2021, with English translation thereof, pp. 1-8.
"Written Opinion of the International Searching Authority (Form PCT/ISA/237) of PCT/CN/2020/137461", mailed on Sep. 10, 2021, pp. 1-4.
Aurélien Jacob et al., "Homologous Recombination Offers Advantages over Transposition-Based Systems to Generate Recombinant Baculovirus for Adeno-Associated Viral Vector Production," Biotechnology Journal, Nov. 2020, pp. 1-11.
M. Laura Fabre et al., "Chapter 11-Baculovirus-Derived Vectors for Immunization and Therapeutic Applications," Emerging and Reemerging Viral Pathogens, vol. 2: Applied Virology Approaches Related to Human, Animal and Environmental Pathogens, Sep. 2019, pp. 1-29.

(Continued)

*Primary Examiner* — Michael D Burkhart
(74) *Attorney, Agent, or Firm* — JCIPRNET

(57) ABSTRACT

Provided are a preparation method and system for a recombinant adeno-associated virus (rAAV) and a recombinant bacmid. The method comprises: first reconstructing a recombinant bacmid containing a recombinant baculovirus genome that produces essential functional elements for an rAAV, at least one of the essential functional elements being inserted into the N-terminal or C-terminal of a locus of an essential gene of the recombinant baculovirus genome; and then transfecting the obtained recombinant bacmid containing the recombinant baculovirus genome that produces the rAAV into a host cell line for culturing to prepare an rAAV. Compared with recombinant baculoviruses obtained by conventional Tn7 recombinant preparations of recombinant bacmid, the recombinant baculovirus obtained by inserting a core element containing Cap, Rep and ITR into two sides of a baculovirus essential gene has a more stable rAAV serial passage production level in a cell and has a higher rAAV yield.

3 Claims, 19 Drawing Sheets

Specification includes a Sequence Listing.

(56) References Cited

OTHER PUBLICATIONS

Pranav Joshi et al., "Advances in Insect Cell Baculovirus Expression Vector Platforms for Production of Recombinant Adeno-Associated Virus Gene Delivery Vectors," Authorea, Apr. 2020, pp. 1-24.

George Aslanidi et al., "An inducible system for highly efficient production of recombinant adeno-associated virus (rAAV) vectors in insect Sf9 cells," PNAS, vol. 106, Mar. 2009, pp. 5059-5064.

Benoît Doublet et al., "Antibiotic marker modifications of λ Red and FLP helper plasmids, pKD46 and pCP20, for inactivation of chromosomal genes using PCR products in multidrug-resistant strains," Journal of Microbiological Methods, vol. 75, Jun. 2008, pp. 359-361.

Verne A. Luckow et al., "Efficient generation of infectious recombinant baculoviruses by site-specific transposon-mediated insertion of foreign genes into a baculovirus genome propagated in *Escherichia coli*," J Virol., vol. 67, Aug. 1993, pp. 4566-4579.

Rob J Noad et al., "Multigene expression of protein complexes by iterative modification of genomic Bacmid DNA," BMC Molecular Biology, Sep. 2009, pp. 1-13.

Richard H Smith et al., "A simplified baculovirus-AAV expression vector system coupled with one-step affinity purification yields high-titer rAAV stocks from insect cells," Molecular therapy, Nov. 2009, pp. 1888-1896.

Masashi Urabe et al., "Insect cells as a factory to produce adeno-associated virus type 2 vectors," Human Gene Therapy, Nov. 2002, pp. 1-16.

Yang Wu et al., "A Recombinant Baculovirus Efficiently Generates Recombinant Adeno-Associated Virus Vectors in Cultured Insect Cells and Larvae," Molecular Therapy: Methods & Clinical Development, vol. 10, Sep. 2018, pp. 38-47.

Seppo Ylä-Herttuala, "Endgame: Glybera Finally Recommended for Approval as the First Gene Therapy Drug in the European Union," Molecular therapy, vol. 20, Oct. 2012, pp. 1831-1832.

\* cited by examiner

SEQUENCE LISTING

<160> NUMBER OF SEQ ID NOS: 17

<210> SEQ ID NO 1
<211> LENGTH: 1035
<212> TYPE: DNA
<213> ORGANISM: Artificial Sequence
<220> FEATURE:
<223> OTHER INFORMATION: P1-FRT-Chol-P2

<400> SEQUENCE: 1

```
atgggaatta gccatggtcc atatgaatat cctccttagt tcctattccg aagttcctat      60
tctctagaaa gtataggaac ttcggcgcgc ctacctgtga cggaagatca cttcgcagaa     120
taaataaatc ctggtgtccc tgttgatacc gggaagccct gggccaactt ttggcgaaaa     180
tgagacgttg atcggcacgt aagaggttcc aactttcacc ataatgaaat aagatcacta     240
ccgggcgtat tttttgagtt gtcgagattt tcaggagcta aggaagctaa aatggagaaa     300
aaaatcactg gatataccac cgttgatata tcccaatggc atcgtaaaga acattttgag     360
gcatttcagt cagttgctca atgtacctat aaccagaccg ttcagctgga tattacggcc     420 ttttttaaaga ccgtaaagaa aataagcac aagtttatc cggcctttat tcacattctt     480
gcccgcctga tgaatgctca tccggaatta cgtatgcaa tgaagacgg tgagctggtg     540 atatgggata gtgttcaccc ttgttacacc gttttccatg agcaaactga aacgttttca     600
tcgctctgga gtgaatacca cgacgatttc cggcagtttc tacacatata ttcgcaagat     660
gtggcgtgtt acggtgaaaa cctggcctat ttccctaaag ggtttattga gaatatgttt     720
```

```
ttcgtctcag ccaatccctg ggtgagtttc accagttttg atttaaacgt ggccaatatg    780
gacaacttct tcgcccccgt tttcaccatg ggcaaatatt atacgcaagg cgacaaggtg    840
ctgatgccgc tggcgattca ggttcatcat gccgtttgtg atggcttcca tgtcggcaga    900
atgcttaatg aattacaaca gtactgcgat gagtggcagg cgggggcgta aggcgcgcca    960
tttaaatgaa gttcctattc cgaagttcct attctctaga aagtatagga acttcgaagc   1020
agctccagcc tacac                                                    1035
```

```
<210> SEQ ID NO 2
<211> LENGTH: 928
<212> TYPE: DNA
<213> ORGANISM: Artificial Sequence
<220> FEATURE:
<223> OTHER INFORMATION: P1-FRT-Gen-P2

<400> SEQUENCE: 2
atgggaatta gccatggtcc atatgaatat cctccttagt tcctattccg aagttcctat     60
tctctagaaa gtataggaac ttcggcgcgc ctacctgtga cggaagatca cttcgcagaa    120
taaataaatc ctggtgtccc tgttgatacc gggaagccct gggccaactt ttggcgaaaa    180
tgagacgttg atcggcacgt aagaggttcc aactttcacc ataatgaaat aagatcacta    240
ccgggcgtat ttttttgagtt gtcgagattt tcaggagcta aggaagctaa aatgttacgc    300
agcagcaacg atgttacgca gcagggcagt cgccctaaaa caaagttagg tggctcaagt    360
atgggcatca ttcgcacatg taggctcggc cctgaccaag tcaaatccat gcgggctgct    420
cttgatcttt tcggtcgtga gttcggagac gtagccacct actcccaaca tcagccggac    480
tccgattacc tcgggaactt gctccgtagt aagacattca tcgcgcttgc tgccttcgac    540
caagaagcgg ttgttggcgc tctcgcggct tacgttctgc ccaggtttga gcagccgcgt    600
agtgagatct atatctatga tctcgcagtc tccggcgagc accggaggca gggcattgcc    660
accgcgctca tcaatctcct caagcatgag gccaacgcgc ttggtgctta tgtgatctac    720
gtgcaagcag attacggtga cgatcccgca gtggctctct atacaaagtt gggcatacgg    780
gaagaagtga tgcactttga tatcgaccca agtaccgcca cctaagtggc agggcggggc    840
gtaaggcgcg ccatttaaat gaagttccta ttccgaagtt cctattctct agaaagtata    900
ggaacttcga agcagctcca gcctacac                                      928
```

```
<210> SEQ ID NO 3
<211> LENGTH: 2217
<212> TYPE: DNA
<213> ORGANISM: Artificial Sequence
<220> FEATURE:
<223> OTHER INFORMATION: Cap9

<400> SEQUENCE: 3
gccgccctgg ctgccgacgg ttatctaccc gattggctcg aggacaacct tagtgaagga     60
attcgcgagt ggtgggcttt gaaacctgga gcccctcaac ccaaggcaaa tcaacaacat    120
caagacaacg ctcgaggtct tgtgcttccg ggttacaaat accttggacc cggcaacgga    180
ctcgacaagg gggagccggt caacgcagca gacgcggcgg ccctcgagca cgacaaggcc    240
tacgaccagc agctcaaggc cggagacaac ccgtacctca gtacaaacca cgccgacgcc    300
gagttccagg agcggctcaa agaagatacg tcttttgggg gcaacctcgg gcagcagtc    360 ttccaggcca aaaagaggct tcttgaacct cttggtctgg ttgaggaagc ggctaagacg    420
```

```
gctcctggaa agaagaggcc tgtagagcag tctcctcagg aaccggactc ctccgcgggt    480
attggcaaat cgggtgcaca gcccgctaaa aagagactca atttcggtca gactggcgac    540
acagagtcag tcccagaccc tcaaccaatc ggagaacctc ccgcagcccc ctcaggtgtg    600
ggatctctta caatggcttc aggtggtggc gcaccagtgg cagacaataa cgaaggtgcc    660
gatggagtgg gtagttcctc gggaaattgg cattgcgatt cccaatggct gggggacaga    720
gtcatcacca ccagcacccg aacctgggcc ctgcccacct acaacaatca cctctacaag    780
caaatctcca acagcacatc tggaggatct tcaaatgaca cgcctactt cggctacagc     840 accccctggg ggtattttga cttcaacaga ttccactgcc acttctcacc acgtgactgg    900
cagcgactca tcaacaacaa ctggggattc cggcctaagc gactcaactt caagctcttc    960
aacattcagg tcaaagaggt tacgacaaac aatggagtca agaccatcgc caataacctt   1020
accagcacgg tccaggtctt cacggactca gactatcagc tcccgtacgt gctcgggtcg   1080
gctcacgagg gctgcctccc gccgttccca gcggacgttt tcatgattcc tcagtacggg   1140
tatctgacgc ttaatgatgg aagccaggcc gtgggtcgtt cgtccttta ctgcctggaa    1200 tatttcccgt cgcaaatgct aagaacgggt aacaacttcc agttcagcta cgagtttgag   1260
aacgtacctt tccatagcag ctacgctcac agccaaagcc tggaccgact aatgaatcca   1320
ctcatcgacc aatacttgta ctatctctca aagactatta cggttctgg acagaatcaa     1380 caaacgctaa aattcagtgt ggccggaccc agcaacatgc tgtccaggg aagaaactac   1440 atacctggac ccagctaccg acaacaacgt gtctcaacca ctgtgactca aaacaacaac   1500
agcgaatttg cttggcctgg agcttcttct tgggctctca atggacgtaa tagcttgatg   1560
aatcctggac ctgctatggc cagccacaaa gaaggagagg accgtttctt tcctttgtct   1620
ggatctttaa tttttggcaa acaaggaact ggaagagaca cgtggatgc ggacaaagtc    1680 atgataacca acgaagaaga aattaaaact actaacccgg tagcaacgga gtcctatgga   1740
caagtggcca caaccacca gagtgcccaa gcacaggcgc agaccggctg ggttcaaaac    1800
caaggaatac ttccgggtat ggtttggcag gacagagatg tgtacctgca aggacccatt   1860
tgggccaaaa ttcctcacac ggacggcaac tttcacccct ctccgctgat gggagggttt   1920
ggaatgaagc acccgcctcc tcagatcctc atcaaaaaca cacctgtacc tgcggatcct   1980
ccaacggcct tcaacaagga caagctgaac tctttcatca cccagtattc tactggccaa   2040
gtcagcgtgg agatcgagtg ggagctgcag aaggaaaaca gcaagcgctg gaacccggag   2100
atccagtaca cttccaacta ttacaagtct aataatgttg aatttgctgt taatactgaa   2160
ggtgtatata gtgaaccccg ccccattggc accagatacc tgactcgtaa tctgtaa      2217

<210> SEQ ID NO 4
<211> LENGTH: 1872
<212> TYPE: DNA
<213> ORGANISM: Artificial Sequence
<220> FEATURE:
<223> OTHER INFORMATION: Rep2

<400> SEQUENCE: 4
gccgccctgg cggggtttta cgagattgtg attaaggtcc ccagcgacct tgacgggcat     60
ctgcccggca tttctgacag ctttgtgaac tgggtggccg agaaggagtg ggagttgccg    120
ccagattctg acttggatct gaatctgatt gagcaggcac ccctgaccgt ggccgagaag    180
ctgcagcgcg actttctgac ggagtggcgc cgtgtgagta aggcccccga ggcccttttc    240
tttgtgcaat ttgagaaggg agagagctac ttccacttac acgtgctcgt ggaaaccacc    300
```

```
gggggtgaaat ccttagtttt gggacgtttc ctgagtcaga ttcgcgaaaa actgattcag      360
agaatttacc gcgggatcga gccgactttg ccaaactggt tcgcggtcac aaagaccaga      420
aacggcgccg gaggcgggaa caaggtggtg gacgagtgct acatccccaa ttacttgctc      480
cccaaaaccc agcctgagct ccagtgggcg tggactaatt tagaacagta tttaagcgcc      540
tgtttgaatc tcacggagcg taaacggttg gtggcgcagc atctgacgca cgtgtcgcag      600
acgcaggagc agaacaaaga gaatcagaat cccaattctg acgcgccggt gatcagatca      660
aaaacttcag ccaggtacat ggagctggtc gggtggctcg tggacaaggg gattacctcg      720
gagaagcagt ggatccagga ggaccaggcc tcatacatct ccttcaatgc ggcctccaac      780
tcgcggtccc aaatcaaggc tgccttggac aatgcgggaa agattatgag cctgactaaa      840 accgccccg actacctggt gggccagcag cccgtggagg acatttccag caatcggatt      900
tataaatttt tggaactaaa cgggtacgat ccccaatatg cggcttccgt ctttctggga      960
tgggccacga aaaagttcgg caagaggaac accatctggc tgtttgggcc tgcaactacc     1020
gggaagacca acatcgcgga ggccatagcc cacactgtgc ccttctacgg gtgcgtaaac     1080
tggaccaatg agaactttcc cttcaacgac tgtgtcgaca agatggtgat ctggtgggag     1140
gaggggaaga tgaccgccaa ggtcgtggag tcggccaaag ccattctcgg aggaagcaag     1200
gtgcgcgtgg accagaaatg caagtcctcg gcccagatag acccgactcc cgtgatcgtc     1260
acctccaaca ccaacatgtg cgccgtgatt gacgggaact caacgacctt cgaacaccag     1320
cagccgttgc aagaccggat gttcaaattt gaactcaccc gccgtctgga tcatgacttt     1380
gggaaggtca ccaagcagga agtcaaagac ttttccggt gggcaaagga tcacgtggtt     1440
gaggtggagc atgaattcta cgtcaaaaag ggtggagcca agaaaagacc cgcccccagt     1500
gacgcagata taagtgagcc caaacgggtg cgcgagtcag ttgcgcagcc atcgacgtca     1560
gacgcggaag cttcgatcaa ctacgcagac aggtaccaaa acaaatgttc tcgtcacgtg     1620
ggcatgaatc tgatgctgtt tccctgcaga caatgcgaga gaatgaatca gaattcaaat     1680
atctgcttca ctcacggaca gaaagactgt ttagagtgct ttcccgtgtc agaatctcaa     1740
cccgtttctg tcgtcaaaaa ggcgtatcag aaactgtgct acattcatca tatcatggga     1800
aaggtgccag acgcttgcac tgcctgcgat ctggtcaatg tggatttgga tgactgcatc     1860
tttgaacaat aa                                                         1872

<210> SEQ ID NO 5
<211> LENGTH: 141
<212> TYPE: DNA
<213> ORGANISM: Artificial Sequence
<220> FEATURE:
<223> OTHER INFORMATION: ITR

<400> SEQUENCE: 5
cctgcaggca gctgcgcgct cgctcgctca ctgaggccgc ccgggcaaag cccgggcgtc       60
gggcgacctt tggtcgcccg gcctcagtga gcgagcgagc gcgcagagag ggagtggcca      120
actccatcac tagggggttcc t                                                 141

<210> SEQ ID NO 6
<211> LENGTH: 370
<212> TYPE: DNA
<213> ORGANISM: Artificial Sequence
<220> FEATURE:
<223> OTHER INFORMATION: HAL(Ac135)
```

<400> SEQUENCE: 6

```
agttattgtg ccgtttgctc acgaaattaa cgacacggga ctttacgagt acgacgtcgt    60
agcttacgtg gacagtgtgc agtttgatgg cgaacaattt gaagagtttg tgcagagttt   120
aatattgccg tcgtcgttca aaaattcgga aaaggtttta tattcaacg aagcgtcgaa    180
aaacaaaagc atgatctaca aggctttaga gtttactaca gaatcgagct ggggcaaatc   240
cgaaaagtat aattggaaaa ttttttgtaa cggtttatt tatgataaaa aatcaaaagt    300
gttgtatgtt aaattgcaca atgtaactag tgcactcaac aaaaatgtaa tattaaacac   360
aattaaataa                                                          370
```

<210> SEQ ID NO 7
<211> LENGTH: 386
<212> TYPE: DNA
<213> ORGANISM: Artificial Sequence
<220> FEATURE:
<223> OTHER INFORMATION: HAR(Ac135)

<400> SEQUENCE: 7

```
tcatttgttt ttaaaattga actggctttta cgagtagaat tctacgcgta aaacacaatc    60
aagtatgagt cataatctga tgtcatgttt tgtacacggc tcataaccga actggcttta   120
cgagtagaat tctacttgta atgcacgatc agtggatgat gtcatttgtt tttcaaatcg   180
agatgatgtc atgttttgca cacggctcat aaactcgctt tacgagtaga attctacgtg   240
taacgcacga tcgattgatg agtcatttgt tttgcaatat gatatcatac aatatgactc   300
atttgttttt caaaaccgaa cttgatttac gggtagaatt ctacttgtaa agcacaatca   360
aaagatgat gtcatttgtt tttcaa                                          386
```

<210> SEQ ID NO 8
<211> LENGTH: 401
<212> TYPE: DNA
<213> ORGANISM: Artificial Sequence
<220> FEATURE:
<223> OTHER INFORMATION: HAL(GP64)

<400> SEQUENCE: 8

```
ggtaacggcc aattcaacgt gacgatgcgc acgtcctcgg gtatgcattt gttaaaaaac    60
acacagctcg ctttaccaaa cgaaagcaaa ggtactaaat atggcgccat tggctgattt   120
gttattccaa gataattaca ataaactga tccgtcgtgg ggtgataact ggcaggtgtc    180
agctttaaat aatcttcaac gttgttgtcg cgcaaaagtc tgcatttttac acgcgttgtt   240
aatcccacga cttttgcatg taaaatcgga tccaaatact gcagaatcgt gtctataatt   300
tctaatggta aacgtatgcg ttttgctcgt gggcgctttg taacgctcga catcctaata   360
acaactaaca caaaactaaa atgatactca atatattgct t                       401
```

<210> SEQ ID NO 9
<211> LENGTH: 406
<212> TYPE: DNA
<213> ORGANISM: Artificial Sequence
<220> FEATURE:
<223> OTHER INFORMATION: HAR(GP64)

<400> SEQUENCE: 9

```
tctcaacaca ctcgctattt ggaacataat catatcgtct cagtagctca aggtagagcg    60
tagcgctctg gatcgtatag atcttgctaa ggttgtgagt tcaagtctcg cctgagatat   120
taaaaaactt tgtaattttta aaattttat tttataatat acaattaaaa actatacaat   180
```

```
tttttattat tacattaata atgatacaat ttttattatt acatttaata ttgtctatta        240
cggtttctaa tcatacagta caaaaataaa atcacaatta atataattac aaagttaact        300
acatgaccaa acatgaacga agtcaattta gcggccaatt cgccttcagc catggaagtg        360
atgtcgctca gactggtgcc gacgccgcca aacttggtgt tctcca                      406
```

<210> SEQ ID NO 10
<211> LENGTH: 409
<212> TYPE: DNA
<213> ORGANISM: Artificial Sequence
<220> FEATURE:
<223> OTHER INFORMATION: HAL(38K)

<400> SEQUENCE: 10

```
tcggcgaacg tgttttgtcc caacgagttt agcgtgacca cgttcacgca atccactatt         60
aaaacgatca acgagacggg aatatatgcc accgcatgca cgccggtcag cagcttgacg        120
ctaattgaac attttgcaac attaaaaaat aacgtgcccg atcacacgct cgttctcgat        180
gtggtcgacc aacagattca gttttcaata ctcgacatta tcaattattt gatttacaat        240
ggctacgtgg atttgttggc cgaataacgc gtatatagac gcttgtacgt tcatcgtagt        300
aatcatttta atacatttga ttgaactaaa catacatctg caatgggtga aagagtcact        360
aaattttgca atggaaaacg gcgataaaga agacagcgac aatgaatag                    409
```

<210> SEQ ID NO 11
<211> LENGTH: 430
<212> TYPE: DNA
<213> ORGANISM: Artificial Sequence
<220> FEATURE:
<223> OTHER INFORMATION: HAR(38K)

<400> SEQUENCE: 11

```
agtttatatt tttatttaat aaaatattgt tcgtaatcca taatgttttg tattatttca         60
ttgtgataat gttcccaatc ttgcacgggg gtggggcatc gtttgacttt gacgtagaaa        120
tcgtacgcgt agttattagt tggcagatcg tcgacaagtg tgatcgactt gaaaaagttt        180 acattttat cgctcaaata tttaattaca atttttggcg atttgggtat attgttgtcg        240
gatcgatgat tgtgaatgtc aaaaacaaat ttattttcaa tgaaacgctt ttttaaattg        300
taatctacaa tagcgttgtg tgaattttga actaaatcag agcgttcttc ttgaacggtg        360
gaaccttcgc tgataatgat atcaaaatag ccttccaaat cgacgtctcg catcgagtgt        420
gctacatgat                                                              430
```

<210> SEQ ID NO 12
<211> LENGTH: 428
<212> TYPE: DNA
<213> ORGANISM: Artificial Sequence
<220> FEATURE:
<223> OTHER INFORMATION: HAL(IE1)

<400> SEQUENCE: 12

```
atcatgacaa tattgcgagt aataataacg cagaaaattt aaaaaaggtt aagaaggagg         60
acggcagcat gcacattgtc gaacagtatt tgactcagaa tgtagataat gtaaagggtc        120 acaatttat agtattgtct ttcaaaaacg aggagcgatt gactatagct aagaaaaaca        180
aagagtttta ttggatttct ggcgaaatta aagatgtaga cgttagtcaa gtaattcaaa        240
aatataatag atttaagcat cacatgtttg taatcggtaa agtgaaccga agagagagca        300
```

```
ctacattgca caataatttg ttaaaattgt tagctttaat attacagggt ctggttccgt    360
tgtccgacgc tataacgttt gcggaacaaa aactaaattg taaatataaa aaattcgaat    420
ttaattaa                                                              428

<210> SEQ ID NO 13
<211> LENGTH: 414
<212> TYPE: DNA
<213> ORGANISM: Artificial Sequence
<220> FEATURE:
<223> OTHER INFORMATION: HAR(IE1)

<400> SEQUENCE: 13
ttatacatat attttgaatt taattaatta tacatatatt ttatattatt tttgtctttt     60
attatcgagg ggccgttgtt ggtgtggggt tttgcataga ataacaatg ggagttggcg     120 acgttgctgc gccaacacca cctcctcctc ctcctttcat catgtatctg tagataaaat    180
aaaatattaa acctaaaaac aagaccgcgc ctatcaacaa aatgataggc attaacttgc    240
cgctgacgct gtcactaacg ttggacgatt tgccgactaa accttcatcg cccagtaacc    300
aatctagacc caagtcgcca actaaatcac caaacgagta aggttcgatg cacatgagtg    360
tttggcccgc aggaagatcg ctaatatcta cgtattgagg cgaatctggg tcgg          414

<210> SEQ ID NO 14
<211> LENGTH: 446
<212> TYPE: DNA
<213> ORGANISM: Artificial Sequence
<220> FEATURE:
<223> OTHER INFORMATION: HAL(GP41)

<400> SEQUENCE: 14
ttttgtgaac gggctcgcta aattgttgcg gttcgctggc agtatcgtcg ttgagcgcca     60
atttcaacgg gatgtattcc acctttttcgt ggttgcccaa ccgatagtag ggcacgtcca    120
aattcatgtt tacaacttat ttgctaacag gaatttatgc aacaaaagtg gtttggcttt    180
gatgagacgc aatttgaaat acttgctgca tttacgctta agattgtatt ccatgcgggc    240
ggcggtgttg tagtcgtacg cgctcgcgct gtgatacacg agccgtaaat tggttgcgtt    300
gcgcaaacac ttggcgcctt gtttgttcga atgctgtttt atgcgtctgt taagattgct    360
cgtgatgccc gtgtacaatt ttccattgtc ttgccgcaga atgtacacgc accacacctt    420
gttggtgtac agagtcgtcg ccatga                                           446

<210> SEQ ID NO 15
<211> LENGTH: 394
<212> TYPE: DNA
<213> ORGANISM: Artificial Sequence
<220> FEATURE:
<223> OTHER INFORMATION: HAR(GP41)

<400> SEQUENCE: 15
ttatgcagtg cgccctttcg tgttcggccg agtggcgtta ggcgcagccg cggcaataat     60
cgcgttggcg tccttgttgt aatttatttg ttgaaaaata aaacgtctta gagtttcgtt    120
ttggaacgcc aattcggtca agctctcctg gcaagcgctt ttggtcaaat gagcggccgg    180
cgaattgacc gcgttggcgg ccgacgttaa gaaggtggcg ttctggaaca tgctgggctg    240
```

```
cttgccggct cgcgtcgcca gctcggccat gtaattgaat atgttggcag acgcagatag    300
cggcgccaaa aacgcaacgt tctcttttaa actcatgact cgcgccctgt tttttcgtt     360 cagcacgtag tggtagtaat cgccgccgcc ggca                                394

<210> SEQ ID NO 16
<211> LENGTH: 385
<212> TYPE: DNA
<213> ORGANISM: Artificial Sequence
<220> FEATURE:
<223> OTHER INFORMATION: HAL(Ac153)

<400> SEQUENCE: 16
tgacataaat atggagaatc aggcaaagat agctgctttg gaagctgaat tggaagaaga    60
aaaaaatcac agtgatcaag tagcttctga aaaccgacag ctgatagaag aaaatactcg   120
tctcaatgaa cagattcaag agttgcagca tcaggtgagg acattggtgc cgcaacgtgg   180
cattacggtt aatcagcaaa ttggccgtga cgacagtgcg ccagccgagc tgaacgagcg   240
ttttcgctca cttgtctatt cgactatttc agagctgttt attgaaaatc gcgttcatag   300
tattcaaaat tatgtttatg ccggaacttc tgctgctagt tcatgtgatg taaatgttac   360
tgttaatttt gggtttgaaa attaa                                          385

<210> SEQ ID NO 17
<211> LENGTH: 332
<212> TYPE: DNA
<213> ORGANISM: Artificial Sequence
<220> FEATURE:
<223> OTHER INFORMATION: HAR(Ac153)

<400> SEQUENCE: 17
tgtgatatga aatgtatata taaaaatgat ggaataaata ataaacattt ttatactttt    60
tatgtttttt ttatttcatg tgattaagaa acttttaaga tggatagtag taattgtatt   120
aaaatagatg taaaatacga tatgccgtta cattatcaat gtgacaataa cgcagataaa   180
gacgttgtaa atgcgtatga cactatcgat gttgaccccca acaaaagatt tataattaat   240
cataatcacg aacaacaaca agtcaatgaa acaaataaac aagttgtcga taaaacattc   300
ataaatgaca cagcaacata caattcttgc at                                  332
```

PREPARATION METHOD AND SYSTEM FOR RECOMBINANT ADENO-ASSOCIATED VIRUS, AND RECOMBINANT BACMID

CROSS-REFERENCE TO RELATED APPLICATION

This application is a 371 of international application of PCT application serial no. PCT/CN2020/137461, filed on Dec. 18, 2020, which claims the priority benefit of China application no. 202011393359.1, filed on Dec. 3, 2019. The entirety of each of the above mentioned patent applications is hereby incorporated by reference herein and made a part of this specification.

TECHNICAL FIELD

The present invention belongs to the field of gene therapies, and more particularly, relates to a preparation method and system for a recombinant adeno-associated virus, and a recombinant bacmid.

RELATED ART

Recombinant adeno-associated virus (rAAV) is one of the most promising vectors in the field of gene therapy due to its characteristics such as wide host range, low immunogenicity, high safety, and ability of mediating the long-term stable expression of exogenous genes in animals.

With the approval of the first recombinant adeno-associated virus (rAAV)-mediated gene therapy drug, there has been an increasing need for technologies of large-scale manufacturing of AAV vectors (Yla Herttuala, S., Mol Ther. 20, 1831 1832, 2012). However, the large-scale production of rAAV remains as a limiting factor in the development of this type of therapy. Hence, in order to overcome this difficulty and the issue of biosafety, a production system has been developed to utilize the ability of baculovirus to infect insect cells, where Rep, Cap and ITR core expression elements are provided and integrated into three different types of baculoviral genomes by Tn7 recombination respectively, and it is necessary to use these three types of recombinant baculoviruses to co-infect insect cells for rAAV preparation (Urabe et al., 2002, Hum. Gene Ther., 13: 1935 1943; US20030148506; US20040197895). On this basis, the above production system is further simplified into a production system for two types of baculoviruses, where Rep and Cap expression cassettes are integrated into one baculovirus (Smith et. al., 2009, Mol. Ther., 17:1888 1896). However, the efficiency of co-infecting cells with two types of baculoviruses is low, and the production capacity of each cell cannot be fully utilized. Moreover, infection is a random process, in which the defect of empty-capsid rAAV particles without nucleic acid easily occurs. It is relatively complicated to optimize the conditions of a preparation process, and the quality of prepared rAAV is unstable among different batches.

Consequently, one-baculovirus systems (One Bac system) are further developed on this basis, mainly including a cell line-dependent One Bac system, a shuttle plasmid-based One Bac system, and a DH10Bac-based One Bac system. The packaging cell line-dependent One Bac system involves: first establishing a packaging cell line that induces the expression of AAV Rep and Cap genes, and then infecting the packaging cell line with a recombinant baculovirus integrated with an ITR core expression element carrying an exogenous gene of interest (GOI) BEV-(ITR-GOI), to induce the expression of the Rep and Cap genes in the cell line to further produce a rAAV (Aslanidi et. al., 2009, Proc. Natl. Acad. Sci., USA, 206: 5059 5064). The shuttle plasmid-based One Bac system involves: constructing the Cap gene, the Rep gene and the ITR core expression element of an AAV together into a shuttle plasmid, integrating an rAAV packaging element, carried on the shuttle plasmid, into a baculoviral genome by Tn7 transposon-mediated recombination, and infecting a host cell with the recombinant baculovirus to produce a rAAV (Yang et al., 2018, Mol Ther Methods Clin Dev. 2018 Jul. 4; 10: 38-47). The DH10Bac-based One Bac system involves: integrating the Cap and Rep genes of AAV into a baculoviral genome (bacmid) in DH10Bac, performing Tn7 transposon-mediated recombination to obtain a recombinant bacmid containing an ITR core element, a Cap gene, and a Rep gene, and infecting a host cell with the recombinant baculovirus (BEV) to produce a rAAV (WU Yang et al., CN201811618542).

However, all the above-mentioned baculovirus systems rely on Tn7 recombination to insert the ITR core element into a locus of a non-essential gene Polh gene, while Rep and Cap expression cassettes are inserted into the locus of the Polh gene or the loci of some other non-essential genes by Tn7 recombination or Red recombination. Due to the problem of easy loss of Tn7 sequences or non-essential genes during passaging process of the baculovirus, the produced BEV shows poor passage stability. Therefore, these systems are not suitable for large-scale batch production and application with very high requirement on stability. Hence, there is still a great need for improvement in the production of gene therapy vector drug.

SUMMARY OF INVENTION

In view of the defects in the prior art or the improvement needs, the present invention provides a preparation method and a system for recombinant adeno-associated virus, and a recombinant bacmid. By inserting at least one of essential functional elements (a Cap gene expression cassette, a Rep gene expression cassette, and a core expression element ITR-GOI carrying an exogenous gene of interest) for producing the recombinant adeno-associated virus into the N-terminal or C-terminal of an essential gene of the recombinant baculoviral genome, the present invention aims to solve the problems in the prior art on insertion of the essential functional element into a non-essential gene locus in the recombinant baculoviral genome, and poor passaging stability of derived BEVs due to the easy loss of the exogenous gene during the passaging process of the baculovirus.

To achieve the object mentioned above, the present invention provides a preparation method for a recombinant adeno-associated virus, including the following steps:

(1) Constructing a recombinant bacmid containing recombinant baculoviral genome for the production of recombinant adeno-associated virus, the recombinant baculoviral genome contains essential functional elements for the production of the recombinant adeno-associated virus, and the essential functional elements include a Cap gene, a Rep gene, and a core expression element ITR-GOI that carries the exogenous gene of interest; and (2) Transfecting the recombinant bacmid from Step (1), which contains the recombinant baculoviral genome for the production of the recombinant adeno-associated virus, into a host cell line for culture;

wherein at least one of the essential functional elements is inserted into a N-terminal or C-terminal of the essential genetic locus of the recombinant baculoviral genome.

Preferably, at least one of the essential functional elements being inserted into the N-terminal or C-terminal of the essential genetic locus of the recombinant baculoviral genome refers to that at least one of the essential functional elements is located within the range of 3 kb of the essential gene expression cassette of the recombinant baculoviral genome.

Preferably, at least one of the essential functional elements is located within the range of 1.5 kb of the essential gene expression cassette.

Preferably, Step (1) specifically involves: the construction of a homologous recombinant vector that contains the essential functional elements for the production of the recombinant adeno-associated virus; or the construction of the homologous recombinant vector and the shuttle plasmid that contain the essential functional elements for the production of the recombinant adeno-associated virus, and integrating three essential functional elements for the production of the recombinant adeno-associated virus into the same recombinant bacmid that contains the recombinant baculoviral genome by using homologous recombination method, so as to acquire the recombinant bacmid of the recombinant baculoviral genome that contains the essential functional elements for the production of the recombinant adeno-associated virus;

wherein the homologous recombinant vector contains the essential genes of the target baculovirus, and the vector carries at least one of the Cap gene expression cassette, the Rep gene expression cassette and the ITR-GOI.

Preferably, the remaining essential functional elements are inserted into loci of non-essential genes of the recombinant baculoviral genome.

Preferably, the locus of the essential gene of the baculoviral genome is selected from Ac6, Ac9, Ac10, Ac17, Ac66, Ac109, Ac139, Ac135, Ac98, Ac147, and Ac128.

Preferably, the locus of the essential gene of the baculoviral genome is selected from Ac135, Ac98(38K), Ac147 (IE1) and Ac128(GP64).

Preferably, the Cap gene expression cassette and the Rep gene expression cassette are inserted into the C-terminal of one essential genetic locus of the recombinant baculoviral genome; and the core expression element ITR-GOI that carries the exogenous gene of interest is inserted into one locus of the non-essential gene of the recombinant baculoviral genome.

Preferably, the Cap gene expression cassette and the Rep gene expression cassette are inserted into the N-terminal or C-terminal of one essential genetic locus of the recombinant baculoviral genome; and the core expression element ITR-GOI that carries the exogenous gene of interest is inserted into the N-terminal or C-terminal of another locus of the essential gene of the recombinant baculoviral genome.

Preferably, a gene sequence of the Cap gene is a codon-optimized sequence according to leaky ribosomal scanning.

Preferably, the gene sequence of the Cap gene is the sequence set forth in SEQ ID No. 1.

Preferably, a gene sequence of the Rep gene is a codon-optimized sequence according to leaky ribosomal scanning.

Preferably, the gene sequence of the Rep gene is the sequence set forth in SEQ ID No. 2.

Preferably, a gene sequence of the core expression element ITR is the sequence set forth in SEQ ID No. 3.

Preferably, Step (1) specifically includes the following substeps:

(1-1) Constructing one or more homologous recombination vectors containing the Cap gene expression cassette, the Rep gene expression cassette, and the core expression element ITR-GOI that carries the exogenous gene of interest; and (1-2) Integrating the Cap gene expression cassette, the Rep gene expression cassette, and the core expression element ITR-GOI that carries the exogenous gene of interest by using the one or more homologous recombination vectors derived from Step (1-1), and inserting the same into the N-terminal or C-terminal of one or more loci of essential genes in the recombinant baculoviral genome, so as to obtain the recombinant bacmid that contains the recombinant baculoviral genome with all the essential functional elements for the production of the recombinant adeno-associated virus.

Preferably, Step (1) specifically includes the following steps:

(1-1) Constructing a homologous recombination vector containing one or two essential functional elements; and inserting AAV essential functional elements in the homologous recombination vector into the N-terminal or C-terminal of one or two loci of essential genes in the baculoviral genome by Red homologous recombination;

(1-2) Constructing a shuttle plasmid containing the remaining essential functional elements; and (1-3) Integrating the Cap gene expression cassette, the Rep gene expression cassette, and the core expression element ITR-GOI that carries the exogenous gene of interest into a baculoviral genome by Tn7 recombination mediated by the shuttle plasmid, to obtain the recombinant bacmid that contains the recombinant baculoviral genome with all the essential functional elements for the production of the recombinant adeno-associated virus.

According to another aspect of the present invention, a recombinant bacmid for preparing a recombinant adeno-associated virus is provided. The recombinant bacmid includes a recombinant baculoviral genome, the recombinant baculoviral genome contains essential functional elements for the production of recombinant adeno-associated virus, and the essential functional elements include the Cap gene, the Rep gene, and the core expression element ITR-GOI that carries the exogenous gene of interest;

wherein at least one of the essential functional elements is inserted into a N-terminal or C-terminal of the essential genetic locus of the recombinant baculoviral genome.

According to another aspect of the present invention, a preparation system for a recombinant adeno-associated virus is provided, including the recombinant bacmid.

Compared with the prior art, the above technical solutions conceived according to the present invention can achieve the following beneficial effects.

(1) In the preparation method for the rAAV provided by the invention, at least one of the essential functional elements (the Cap gene expression cassette, the Rep gene expression cassette and the core expression element ITR-GOI with the exogenous gene of interest) for the production of the recombinant adeno-associated virus is inserted into the N-terminal or C-terminal of the essential gene in the recombinant baculoviral genome, which not only does not affect the expression of the essential gene, but also well solves the technical problem of poor passage stability of the derived BEV due to the easy loss of the exogenous gene during baculovirus passaging process in the prior art where the rAAV essential functional elements are inserted into the loci of the non-essential genes of the recombinant baculoviral genome. Stability is a key factor that limits the large-scale scale-up (such as a scale of 2000 L) of the system for preparing the AAV from the baculovirus. The present invention solves problem on the passage stability of the BEV and makes it possible to scale up the preparation of the AAV on a large scale.

(2) In the recombinant bacmid containing the recombinant baculoviral genome with the essential functional elements for the rAAV production according to the present invention, because one or more of the ITR-GOI, Rep gene and Cap gene are loaded on the N-terminal or C-terminal of one or more essential genes of the recombinant baculoviral genome, the passage stability and rAAV yield of the recombinant baculovirus containing all the functional elements for producing the rAAV are significantly improved; and the present invention shows good compatibility with the existing system for preparing the rAAV from baculovirus, and significantly increases the overall stability of the prepared recombinant baculoviral BEV.

(3) In the preferred embodiment of the present invention, three essential gene elements for producing the recombinant adeno-associated virus are all inserted into one terminus of the locus of the essential gene in the recombinant baculoviral genome, which greatly improves the passage stability of the recombinant baculovirus and the yield of the recombinant adeno-associated virus.

DESCRIPTION OF EMBODIMENTS

For clearer understanding of the objects, technical solutions and advantages of the present invention, the following further describes the present invention in detail in conjunction with the accompanying drawings and embodiments. It should be understood that the specific embodiments described herein are merely for the purpose of explaining the present invention, rather than limiting the present invention.

A baculovirus derived from *Autographa californica* multiple nucleopolyhedrovirus (AcMNPV) has a genome of about 134 kb in total length, with about 156 open reading frames. 62 genes among these genes can be classified as (possible) non-essential genes. In known baculoviral systems, the Cap gene, Rep gene and core expression element ITR of AAV are individually or together inserted into the loci of non-essential genes such as Polh, Chia, Cath, egt, p10, and ctx. During baculoviral passaging process, an exogenous gene is prone to loss to cause poor passage stability of the resulting BEV. The other 94 genes are considered to be essential genes for cell culture and proliferation, wherein some of these genes, such as Ac 100 (P6.9), Ac 89 (VP39 capsid), Ac80 (GP41 tegument)), Ac98 (38K), Ac142, Ac144, Ac92 (P33), Ac54 (VP1054), Ac77 (VLF-1), Ac104 (VP80), Ac9 (PP78/83), are proteins associated with baculoviral nucleocapsids. Once these genes are deleted or mutated, the baculovirus cannot exist stably. Some of these genes, such as Ac94 (ODV E25), Ac109 (ODVEC43) and Ac143 (ODV E18) are envelope proteins of the baculovirus, and once these genes are deleted, the baculovirus cannot exist stably. Some of these genes, such as Ac17, Ac34, Ac36, Ac38, Ac139, and Ac153, are proteins associated with BV yield, and once these genes are deleted, the BV titer of the baculovirus would decrease to $1/100$-$1/1000$. These essential genes are relatively stable during baculoviral passaging process and are not prone to loss.

Figure 1:
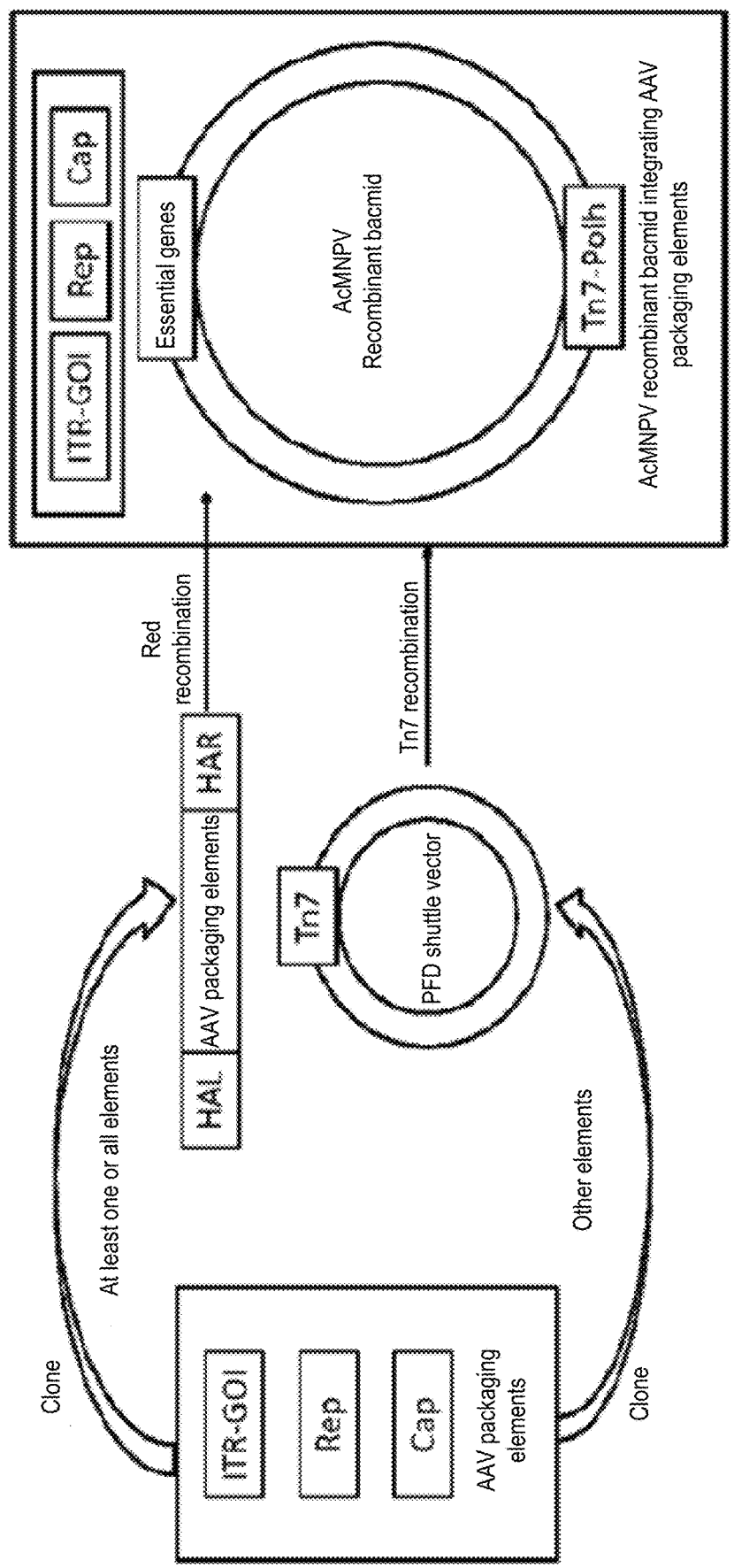
FIG. 1 is a schematic flowchart for preparing a recombinant adeno-associated virus according to the present invention.

The present invention provides a preparation method for a recombinant adeno-associated virus. As shown in FIG. 1, the preparation method includes the following steps:

(1) Constructing a recombinant bacmid containing a recombinant baculoviral genome for the production of the recombinant adeno-associated virus, the recombinant baculoviral genome contains essential functional elements for the production of the recombinant adeno-associated virus, and the essential functional elements include a Cap gene, a Rep gene, and a core expression element ITR-GOI that carries the exogenous gene of interest; and (2) Transfecting the recombinant bacmid obtained from Step (1), which contains the recombinant baculoviral genome for the production of the recombinant adeno-associated virus, into a host cell line for culture;

wherein at least one of the essential functional elements is inserted into a N-terminal or C-terminal of the essential genetic locus of the said recombinant baculoviral genome. The N-terminal or C-terminal of the locus of the essential gene in the present invention refers to that the essential functional element is located within the range of 3 kb, preferably the range of 1.5 kb, of the essential gene expression cassette of the recombinant baculoviral genome.

In some embodiments, Step (1) specifically involves: constructing of a homologous recombinant vector that contains the essential functional elements for the production of the recombinant adeno-associated virus; or constructing of the homologous recombinant vector and the shuttle plasmid that contain the essential functional elements for the production of the recombinant adeno-associated virus, and integrating three essential functional elements for the production of the recombinant adeno-associated virus into the same recombinant bacmid that contains the recombinant baculoviral genome by using a homologous recombination method, so as to acquire the recombinant bacmid of the recombinant baculoviral genome that contains the essential functional elements for the production of the recombinant adeno-associated virus. The homologous recombinant vector includes a targeted baculoviral essential gene, and the vector carries at least one of Cap gene expression cassette, a Rep gene expression cassette, and an ITR-GOI.

In some embodiments, the homologous recombination is Red recombination and/or Tn7 homologous recombination.

The Tn7 transposon-mediated recombination is a fast and efficient method for constructing an exogenous gene onto the recombinant baculoviral genomes, where a Tn7 transposon identification sequence needs to be introduced into the recombinant baculoviral genome first. In addition, it is not suitable for recombination at a plurality of different sites simultaneously or multiple times. At present, it is still a relatively complicated and tedious work to efficiently transform the recombinant baculoviral genome.

Red recombination, as an efficient recombination method at a bacterial level, can be used to rapidly transform the recombinant baculoviral genome in *Escherichia coli* (DH10Bac). In the Red recombination, a linear DNA fragment, which carries a homologous arm and is introduced into a cell, is homologously recombined with the specific target sequence of the genome by using 2 phage Red recombinase (composed of three proteins, including Exo, Beta and Gam), thereby realizing the replacement of the gene of interest (refer to Doublet et al., 2008, J Microbiol Methods., 75(2): 359-61). To facilitate the screening of recombinants, a chloramphenicol (Chol) resistance gene expression cassette (SEQ ID No. 1) flanked with FRT sequences or a gentamycin (Gen) resistance gene expression cassette (SEQ ID No. 2) flanked with FRT sequences is introduced for the subsequent removal of the resistance gene by a pCP20 plasmid (a temperature-sensitive plasmid expressing Flp recombinase), which can be used to perform a series of gene deletion or insertion in a bacmid genome by consecutively using the resistance gene multiple times.

In the preparation method for the recombinant adeno-associated virus according to the present invention, one, two or three of the essential functional elements for producing the recombinant adeno-associated virus can be inserted into the N-terminal or C-terminal of the locus of the essential gene of the recombinant baculoviral genome, in order to increase the passage stability of the baculovirus by virtue of the characteristic that the essential gene locus is not easily lost during baculoviral passaging, thereby increasing overall stability and yield in the preparation of the recombinant adeno-associated virus. If the essential functional elements are not completely inserted into the loci of the essential genes in the recombinant baculoviral genome, the remaining essential functional elements may also be inserted into the loci of the non-essential genes in the recombinant baculoviral genome. In a preferred solution, the three essential functional elements are all inserted into the N-terminal or C-terminal of the loci of the essential genes in the recombinant baculoviral genome.

The essential gene of the baculoviral genome in the present invention is defined as a gene whose inactivation in or removal from the baculoviral genome severely affects the growth ability and/or stable existence of the baculovirus in insect cell cultures. In some embodiments, the essential genetic locus of the baculoviral genome is selected from Ac6 (3089 . . . 3721), Ac17(13738 . . . 14232), Ac9(5287 . . . 6918), Ac66(55292 . . . 57718), Ac109(94721 . . . 95893), Ac98(85021 . . . 85983), Ac139(121205 . . . 122554), Ac135(116492 . . . 117391), Ac10(6917 . . . 7735), 1E1 (127198 . . . 128946) and GP64(108179 . . . 109717), wherein IE1 is also Ac147, and GP64 is also Ac128.

In an embodiment of the present invention, the AAC packaging elements are inserted into the C-terminal of four essential genes, including Ac135, Ac98 (38K), Ac147 (IE1), and Ac128(GP64). Compared with a recombinant baculovirus derived from a recombinant bacmid prepared by traditional Tn7 recombination, the recombinant baculovirus prepared by inserting Cap, Rep and ITR core elements into the C-terminal of the essential genes in the baculovirus shows a stabler level of rAAV production after serial passages in cells, with a higher rAAV yield. However, a dramatic drop is shown in the level of rAAV production in cells with serial passages of the recombinant baculoviruses obtained by inserting AAV packaging elements into the C-terminal of the essential genes Ac80 (GP41) and Ac153 of baculovirus. Through analysis, the reason may lie in that inserting the AAV packaging elements into the C-terminal of the essential genes Ac80 (GP41) and Ac153 of the baculovirus destroys promoter regions of the downstream essential genes Ac79 and Ac154, which affects the expression of the genes Ac79 and Ac154, leading to the dramatic drop in the level of rAAV production in cells with serial passages of the obtained recombinant baculoviruses. Hence, it is speculated that the AAV packaging elements should be appropriately inserted into the N-terminal or C-terminal of the essential genes of the baculovirus without affecting the expression of the upstream and downstream essential genes, and the loci of the essential genes of the baculovirus may also be selected from Ac6, Ac9, Ac10, Ac17, Ac66, Ac109 and Ac139.

The loci of the non-essential genes in the recombinant baculoviral genome of the present invention are one or more selected from Chia, Cath, Ac124, p10, p26, p'74, ctx, egt, 39k, orf51, gp37, iap2 and odv e56. Preferably, the loci of the non-essential genes are selected from Chia and/or Cath.

In some embodiments, the Cap gene expression cassette and the Rep gene expression cassette are inserted into the N-terminal or C-terminal of the locus of one essential gene in the recombinant baculoviral genome; the core expression element ITRGOI with the exogenous gene of interest is inserted into the locus of one none-essential gene or the N-terminal or C-terminal of the locus of the non-essential gene in the recombinant baculoviral genome.

In some other embodiments, the Cap gene expression cassette and the Rep gene expression cassette are inserted into the N-terminal or C-terminal of the locus of one essential gene in the recombinant baculoviral genome; the core expression element ITR-GOI with the exogenous gene of interest is inserted into the N-terminal or C-terminal of the locus of another essential gene in the recombinant baculoviral genome.

In a preferred embodiment, in the preparation method for the rAAV, a Cap gene sequence in the Cap gene expression cassette is a condon-optimized sequence according to leaky ribosome scanning, preferably, for example, the sequence set forth in SEQ ID No. 3. A Rep gene sequence in the Rep gene expression cassette is a codon-optimized sequence according to leaky ribosome scanning, preferably, for example, the sequence set forth in SEQ ID No. 4. A gene sequence of the core expression element ITR is preferably the sequence set forth in SEQ ID No. 5, for example.

Figure 2:
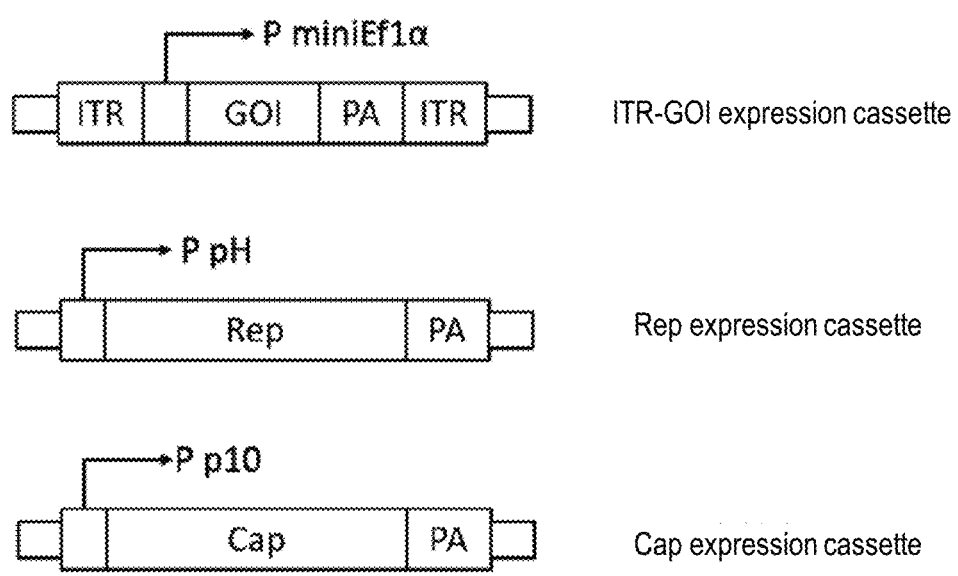
FIG. 2 is a schematic diagram of expression cassettes of essential functional elements of the recombinant adeno-associated virus according to the present invention.

The recombinant bacmid described in the present invention is derived from the genome of the baculovirus AcMNPV, and contains the expression cassettes of the AAV Cap and Rep genes essential for the production of rAAV. The expression cassettes of functional protein components essential for the production of adeno-associated viruses are located downstream P10 or PH promoters and are regulated thereby, as shown in FIG. 2.

In some embodiments: Step (1) specifically includes the following sub-steps:
(1-1) Constructing one or more homologous recombination vectors containing the Cap gene expression cassette, the Rep gene expression cassette, and the core expression element ITR-GOI that carries the exogenous gene of interest; and
(1-2) Integrating the Cap gene expression cassette, the Rep gene expression cassette, and the core expression element ITR-GOI with the exogenous gene of interest by using the one or more homologous recombination vectors derived from Step (1-1), and inserting the same into a N-terminal or C-terminal of one or more loci of essential genes in the recombinant baculoviral genome to obtain the recombinant bacmid containing the recombinant baculoviral genome with all the essential functional elements for producing the recombinant adeno-associated virus.

In some embodiments, Step (1-2) uses the one or more homologous recombination vectors derived from Step (1-1), and the Cap gene expression cassette, the Rep gene expression cassette, and the core expression element ITR-GOI with the exogenous gene of interest are inserted into a N-terminal or C-terminal of one or more loci of essential genes in the recombinant baculoviral genome by Red homologous recombination for integrating.

In various constructs, the vector may include sequences from a virus such as a baculovirus, such as, but not limited to, *Autographa californica* multiple nucleopolyhedrovirus (AcMNPV).

In some embodiments, a homologous recombination vector including a capsid protein gene expression cassette (Cap) and a Rep gene expression cassette (Rep) of the rAAV and a homologous recombination vector containing an ITR core element (ITR-GOI) with an exogenous gene of interest (GOI) are first constructed respectively; then, the Cap and Rep expression cassettes are integrated into a N-terminal or C-terminal of a locus expression cassette of one essential gene in the baculoviral genome by first homologous recombination, and then, the ITR-GOI is integrated into a N-terminal or C-terminal of a locus expression cassette of another essential gene in the baculoviral genome described above by second homologous recombination, to obtain a recombinant bacmid containing the recombinant baculoviral genome with the functional protein components and ITR core element essential for the production of the rAAV.

In some embodiments, a homologous recombination vector containing the Cap gene expression cassette and the Rep gene expression cassette is electrotransformed into DH10Bac/pKD46 electrocompetent cells, to obtain a DH10Bac strain containing the Cap gene expression cassette and the Rep gene expression cassette, with the Cap and Rep gene expression cassettes inserted into the N-terminal or C-terminal of one essential gene expression cassette in the baculoviral genome; then a homologous recombination vector including the core expression element ITR-GOI containing the exogenous gene of interest is electroporated into a DH10Bac strain containing the Cap gene expression cassette and the Rep gene expression cassette, so as to insert the core expression element ITR-GOI containing the exogenous gene of interest into the N-terminal or C-terminal of another essential gene expression cassette in the baculoviral genome, thereby obtaining a recombinant bacmid containing the recombinant baculoviral genome for producing the recombinant adeno-associated virus.

In some other embodiments, Step (1) specifically includes the following steps:
(1-1) Constructing a homologous recombination vector containing one or two of the essential functional elements; then inserting essential functional elements in the homologous recombination vector into a N-terminal or C-terminal of one or two loci of essential genes in the baculoviral genome in *Escherichia coli* by Red homologous recombination;
(1-2) Constructing a shuttle plasmid containing the remaining essential functional elements; and
(1-3) Integrating the Cap gene expression cassette, the Rep gene expression cassette, and the core expression element ITR-GOI that carries the exogenous gene of interest into a baculoviral genome by Tn7 recombination mediated by the shuttle plasmid, to obtain the recombinant bacmid that contains the recombinant baculoviral genome with all the essential functional elements for the production of the recombinant adeno-associated virus.

In some embodiments, a homologous recombination vector including a capsid protein gene expression cassette (Cap) and a Rep gene expression cassette (Rep) of the rAAV and a shuttle vector containing an ITR core element (ITR-GOI) with an exogenous gene of interest (GOI) are first constructed; then, the Cap and Rep expression cassettes are inserted into a N-terminal or C-terminal of a locus of an essential gene in the baculoviral genome by Red homologous recombination; and then, the ITR-GOI in the shuttle vector is inserted into an attTn7 site in the baculoviral genome described above by Tn7 recombination, to obtain a recombinant bacmid containing the recombinant baculoviral genome with the functional protein components and ITR core element essential for the production of the rAAV.

In some embodiments, a homologous recombination vector containing an ITR core element (ITR-GOI) with an exogenous gene of interest (GOI) and a shuttle vector containing a capsid protein gene expression cassette (Cap) and a Rep gene expression cassette (Rep) of the rAAV are first constructed; then, the ITR-GOI is inserted into a N-terminal or C-terminal of a locus of an essential gene in the baculoviral genome by Red homologous recombination; and then, the Cap and Rep expression cassettes in the shuttle vector are inserted into an attTn7 site in the baculoviral genome described above by Tn7 recombination, to obtain a recombinant bacmid containing the recombinant baculoviral genome with the functional protein components and ITR core element essential for the production of the rAAV.

In some embodiments, the shuttle plasmid is based on a pfast. Bac. Dual plasmid, which contains one or two genes of the Rep gene expression cassette, the Cap gene expression cassette, and the ITR-GOI core expression element of the adeno-associated virus.

In some embodiments, the recombinant bacmid containing the recombinant baculoviral genome is derived from AcMNPV E2 (with a genomic sequence such as: Genbank accession No. KM667940.1), AcMNPV cacmid (bMON14272), a structure reference may be made to a reference document (Luckow et al., J. Virol, 1993.67(8): 4566 79).

The packaging of rAAV mainly requires three main essential functional elements: the genome of rAAV (i.e., the ITR core expression element), the Rep functional gene of AAV, and the Cap functional gene of AAV. In addition, other functional protein components such as AAP may also be included, and AAP gene has a certain promoting effect on increasing the packaging efficiency. Therefore, based on the same idea and in order to further increase the packaging efficiency of the recombinant adeno-associated virus, other functional protein components such as APP other than the essential functional elements may also be integrated into the recombinant bacmid, specifically, inserted into the loci of non-essential genes or the N-terminal or C-terminal of the loci of essential genes in the recombinant bacmid genome.

In most of the current baculovirus systems for preparing rAAV, the recombinant baculovirus carrying exogenous genes (the Rep gene, Cap gene or ITR core expression element of AAV) is inserted into a polyhedron (Polh) site of a non-essential gene of the baculovirus; and the commercial Bac-to Bac system is usually used in order to facilitate the construction of recombinant baculoviruses. The principle of the Bac to Bac system is as follows: first, an exogenous gene is constructed into a shuttle plasmid; then the recombinant shuttle plasmid is transformed into *E. coli* containing the recombinant bacmid; and the exogenous gene carried by the recombinant shuttle plasmid is integrated to the recombinant bacmid by Tn7 transposon-mediated recombination at a bacterial level. Then, a recombinant bacmid DNA extracted and obtained from the aforementioned *E. coli* is used to transfect insect cells, and a recombinant baculovirus BEV carrying the exogenous gene is then rescued. In this system, this macromolecular circular DNA that can replicate and reproduce in *E. coli*, replicate in insect cells and package a recombinant baculovirus is called bacmid. The bacmid carries an origin of bacterial replication, an antibiotic resistance gene, a recombinant baculoviral genome and a Tn7 recombination cloning site. The earliest developer, Luckow et al., of this system chose the polyhedron gene (Polh) site as the Tn7 recombination cloning site (Luckow et al., 1993, J. Virol., 67(8): 4566-4579).

Nowadays, there are also some people who choose to insert expression cassettes (Rep and Cap gene expression cassettes) of essential functional protein components for rAAV into some non-essential loci (CN201811618542; CN201280046259) such as ctx, egt, 39k, orf51, pg37, iap2, and odv e56 (Noad et al., 2009, BMC Molecular Biology, 10: 87). There are a plurality of origin sites of replication in the baculoviral genome. During the proliferation process of baculovirus, its genome replicates in the form of multiple origins, and some non-essential gene deletions occurs for BEV after multiple passages. Therefore, a BEV produced by inserting the exogenous gene into a locus of a non-essential gene shows poor passage stability, and the gene of interest is prone to loss. In addition, all current baculovirus systems depend on Tn7 recombination to insert the ITR core expression element, where a pair of Tn7 transposon identification sequences requires to be introduced into the recombinant baculoviral genome. During passaging process of the baculovirus, Tn7 is unstable and would be lost easily, leading to poor passage stability of the produced BEV. As a result, it is not suitable for large-scale batch production and application with high stability requirements, and there is still a great demand for improvement in the production of carrier drugs for gene therapy.

In the recombinant bacmid containing the recombinant baculoviral genome for producing the rAAV according to the present invention, because at least one of the ITR-GOI, Rep gene and Cap gene is loaded on the N-terminal or C-terminal of the essential genes, the overall stability of the prepared recombinant baculovirus BEV significantly increases.

According to the present invention, a host cell line is transfected with the obtained recombinant bacmid containing the recombinant baculovirus genome with the functional protein components and ITR core element, that are essential for producing the rAAV, and then cultured to obtain the recombinant baculovirus. Specifically, the obtained recombinant bacmid is transfected into a corresponding host cell line to prepare the rAAV, including but not limited to the following methods.

Extracting transfection: the DNA of the recombinant bacmid is extracted and purified from *Escherichia coli* by using a kit, and then transfected into the host cell line.

Direct infection: the recombinant bacmid is transfected into the host cell line to obtain a recombinant baculovirus BEV, and then the BEV is used to directly transfect the corresponding host cell line.

The recombinant bacmid containing the baculovirus genome described in the present invention contains the expression cassettes of functional protein components essential for producing the rAAV and the expression cassette of ITR core element. In some embodiments, the recombinant bacmid containing the baculoviral genome is a baculovirus with Chia and Cath genes (CC for short) deletions. The expression cassettes of functional protein components essential for producing the rAAV and the expression cassette of ITR core element are inserted into one or more loci of essential genes in the recombinant bacmid. The essential genes are selected from Ac135, Ac98 (38K), Ac147(IE1), Ac128(GP64), Ac6, Ac9, Ac10, Ac17, Ac66, Ac109, and Ac139.

The present invention further provides a recombinant bacmid for preparing a recombinant adeno-associated virus. The recombinant bacmid includes a recombinant baculoviral genome. The recombinant baculoviral genome contains essential functional elements for producing the recombinant adeno-associated virus; and the essential functional elements include a Cap gene, a Rep gene, and a core expression element ITR-GOI with an exogenous gene of interest, wherein at least one of the essential functional elements is inserted into the N-terminal or C-terminal of a locus of an essential gene in the recombinant baculovirus genome.

The present invention further provides a preparation system for a recombinant adeno-associated virus, including the recombinant bacmid defined as above.

Examples are as follows.

Example 1

Preparation of rAAV by Using DH10Bac Cap Rep (Ac135) Tn7(ITR GOI)

This example included a homologous recombinant vector and a shuttle vector. The homologous recombinant vector targeted an essential gene Ac135, and included an expression cassette of a functional protein component essential for producing the rAAV, a Cho1 expression cassette and an ETL-EGFP expression cassette, wherein the Cho1 expression cassette served as a positive clone selection marker for Red homologous recombination, and the ETL-EGFP expression cassette was used for TCID50 titration test of BEV. The shuttle vector contained an expression cassette of a core expression element ITR-GOI of the rAAV.

With the preparation system for the rAAV in this example, the preparation method for the rAAV included the following steps.

1.1 A homologous recombinant vector containing the expression cassettes of Cap and Rep genes as the essential functional elements of AAV were constructed. Then, the essential functional elements in the homologous recombinant vector were inserted into the C-terminus of the loci of one or two essential genes in the baculoviral genome in *Escherichia coli* by Red homologous recombination, with the specific steps as follows.

1.1.1 A homologous recombinant vector which contained the capsid protein gene expression cassette (Cap) and Rep gene expression cassette (Rep) of rAAV and targeted the essential gene Ac135 gene was constructed. First, we used a wild-type AcMNPV bacmid DNA as a template, an upstream homologous arm fragment HAL(Ac135) (SEQ ID No. 6) was amplified by using primers (HAL(135) F: agttattgtgccgtttgctca and HAL(135) R: ttatttaattgtgtttaatat-taca), and a downstream homologous arm fragment HAR (Ac135) (SEQ ID No. 7) was amplified by using primers (HAR(135) F: tcatttgtttttaaaattga and HAR(135) R: ttgaaaaacaaatgacatcatct).

1.1.2 Then, DNA fragments, including the upstream homologous arm, the downstream homologous arm, a chloramphenicol resistance gene expression cassette (P1-FRTChlo-P2), a Cap9 gene expression cassette (P10-Cap9-PA), and a Rep2 gene expression cassette (PH-Cap9-PA), were cloned together into a pUC57 vector to obtain a homologous recombinant vector pUC57 HAL(Ac135) P1 FRT Chol P2 ETL EGFP PA Cap9KC Rep2 HAR(Ac135) targeting the Ac135 gene.

1.1.3 The homologous recombinant vector obtained in Step 1.1.2 was double-digested with restriction endonucleases PmeI and AvrII, to harvest a linear DNA fragment HAL(Ac135)-P1-FRT-Chol-P2-ETL-EGFP-PA-Cap9KC-Rep2-HAR(Ac135). Then, the DNA fragment was electrotransformed into DH10Bac/pKD46 competent cells, and spread on three resistance types of LB plates with kanamycin, tetracycline and chloramphenicol. After 48-hour inverted culture at 37° C., blue colonies were picked up and shook. Bacmid DNAs were extracted, identified by PCR identification, screened for positive clones, and verified by sequencing. Screened positive strains were named as DH10Bac-P1-FRT-Chol-P2-ETL-EGFP-PACap9KC-Rep2 (Ac135), in which the Rep and Cap expression cassettes were located at 2625 bp at the C-terminal of the baculovirus essential gene Ac135 gene.

1.2 A shuttle vector containing the ITR core element (ITR-GOI) was constructed. In this example, the ITR core expression element used a red fluorescent protein (mcherry) expression cassette. That is, the expression of mcherry was controlled by a miniEfla promoter, which was convenient for detecting the activity of rAAV. The ITR and the red fluorescent protein expression cassette (GOI) were constructed into the shuttle vector pFastDual.

1.3 The shuttle vector constructed in Step 1.2 was transformed into DH10Bac P1 FRT Chol P2 ETL EGFPPA Cap9KC Rep2(Ac135) competence, and the ITR-GOI was inserted into a site Tn7 in the recombinant bacmid containing the recombinant baculoviral genome obtained from the aforementioned Step 2 by Tn7 recombination, to finally obtain a recombinant bacmid, numbered AC20-313, containing the recombinant baculoviral genome with the functional protein components essential for producing the rAAV and the ITR core element.

1.4 The recombinant bacmid AC20-313 containing the recombinant baculoviral genome with the functional protein components essential for producing the rAAV and the ITR core element obtained from Step 1.3 was transfected into a host cell line and cultured to obtain a recombinant baculovirus.

DNA of the recombinant bacmid were extracted and transfected into Sf9 insect cells to prepare recombinant baculovirus BEVs and rAAV. The transfected Sf9 insect cells successfully produced BEV. BEV were replicated and proliferated in large numbers for further infection, leading to obvious cytopathic effects (CPE) in Sf9 cells. The apparent expressions of green fluorescent proteins (GFP) and red fluorescent proteins could be observed under the fluorescence microscope. The culture supernatant of Sf9 cells with CPE was collected, which contained a large amount of BEV, i.e., the 0th passage of BEV (P0); and Sf9 cells containing a large amount of rAAV were collected at the same time. Sf9 cells cultured in suspension were infected with the prepared BEV-P0 at a multiplicity of infection (MOI) of 3. After 72 hours of infection, the cell activity decreased to below 50%. The cell culture solution was centrifuged at 1000 g for 5 min, and the culture supernatant and cell pellets were collected respectively. The supernatant was labeled as the first passage BEV-P1, and the cells were labeled as BEV-P0-packaged rAAV.

The stability of the recombinant baculoviruses produced in this system and the yield stability of AAVs was tested.

First, a corresponding recombinant baculovirus was obtained, as a control, according to the method in the patent CN106544325B, and numbered 9KC 142A(PFD ITR CMV EGFP PA)9KC 142A. Specifically, the capsid protein gene expression cassette (Cap9) and Rep gene expression cassette (Rep) of rAAV and an ITR GOI were constructed together on a shuttle vector, which was then inserted into a locus of a non-essential gene Polh by Tn7 recombination to obtain a recombinant bacmid containing the recombinant baculovirus genome, and finally transfected into Sf9 cells to obtain recombinant baculovirus.

In order to further analyze the stability of the system in this example, the titers of BEV and AAV were detected by the Q-PCR method in this and the following examples. The method was cited from the patent CN108699567A. The BEV Cap Rep(Ac135) Tn7(ITR GOI) prepared in this example was serially passaged at the same MOI to infect the Std cells to obtain BEV of passages P2, P3, P4, P5, . . . , and P10. The passage stability of the recombinant baculoviruses was tested. The titers of BEV in all the passages were measured by using the quantitative PCR (qPCR) method, and the titer unit was VG/ml (VG, virus genomes). The total baculovirus titers were measured by using a pair of primers (Q GP64 F: AACTTGGACATTACCCCGCC and Q GP64 R: CCGTTGTACGCATACGCCTG) corresponding to the gp64 gene; the titers of the baculoviruses containing the Rep and Cap expression cassettes were measured by using a pair of qPCR primers (Q Rep F: GAACAAGGTGGTGGACGAGT and Q Rep R: ATT-CAAACAGGCGCTTAAAT) corresponding to the Rep sequence; and the titers of the baculoviruses containing the ITR GOI were measured by using a pair of primers (Q Tn7 F: tcgtattagcttacgacgctaca and Q Tn7 R: tagttgggaactgg-gagggg) corresponding to the Tn7 sequence. Based on the ratios of Tn7/GP64 and REP/GP64, the passage stability of the exogenous gene fragments (the Rep/Cap expression cassettes and the ITR-GOI expression cassette) in the BEV was evaluated. If the ratios were constant, it indicated good passage stability of the Rep/Cap expression cassettes and the ITR-GOI expression cassette. If the ratios decreased significantly with the increase of the number of passages, it indicated poor stability of the inserted exogenous fragments. The passage of multiplicity of infection (MOI) was calculated by using the total BEV titer, i.e., the Q-PCR titer of GP64, throughout the passaging process.

In another aspect, evaluating the passage stability of the recombinant baculovirus involved the packaging efficiency and supernatant titer of the recombinant adeno-associated virus (rAAV). The titers of rAAVs in all passages were measured in VG/by qPCR method, and the titer unit was VG/ml (VG, virus genomes). The titers of rAAV were detected by using a pair of primers (Q ITR F: GGAACCCCTAGTGATGGAGTT and Q ITR R: CGGCCTCAGTGAGCGA) targeting the ITR sequence or a pair of primers (Q WPRE F: CCGTTGTCAGGCAACGTG and Q WPRE R: AGCTGACAGGTGGTGGCAAT) targeting the WPRE sequence. The results of detection were as follows.

Figure 3:
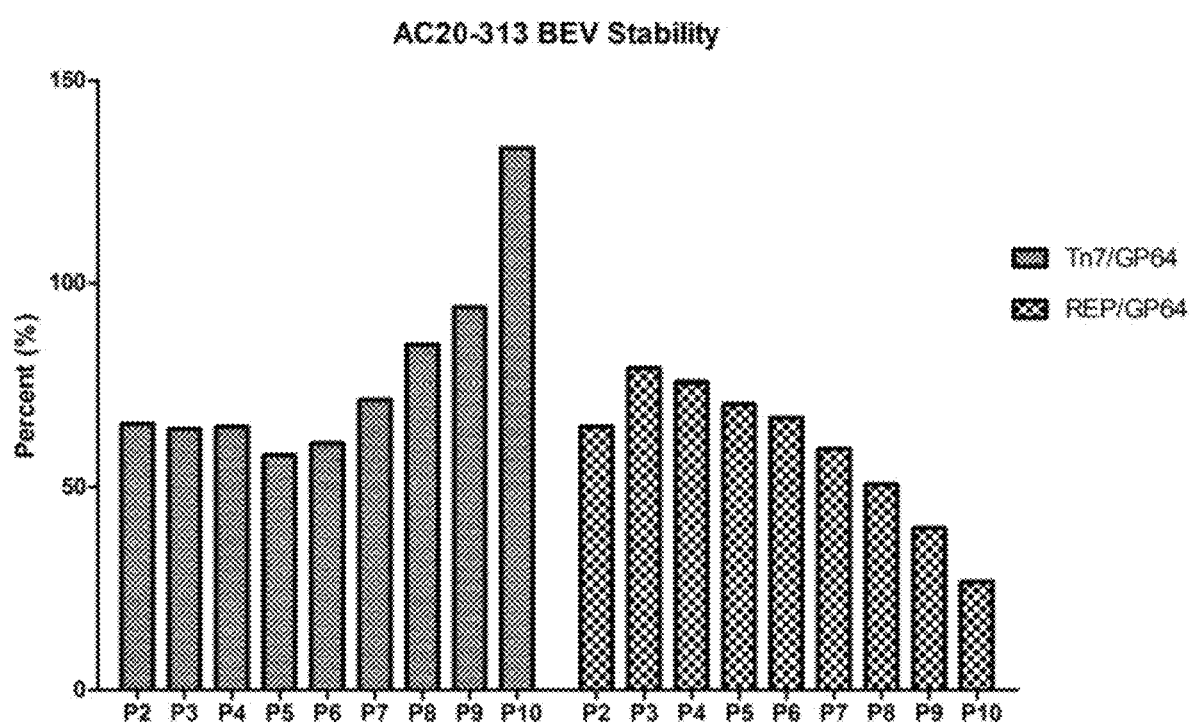
FIG. 3 shows the stability of different passages of AC20 313 BEV constructed according to Example 1.

FIG. 3 shows the stability of AC20 313 BEVs in different passages. The Rep and Cap expression cassettes of rAAV were placed at the C-terminal of the essential gene Ac135 of baculovirus, and the bacmid was numbered AC20-313. The stability of BEV in passages P2-P10 was detected by Q-PCR. The percentage of Tn7/GP64 represented the stability of the ITR-GOI expression cassettes on the BEV, and the percentage of REP/GP64 represented the stability of Rep and Cap expression cassettes on the BEV. Good stability was shown based on the analysis of the stability results of BEV in different passages in the histogram.

Figure 4:
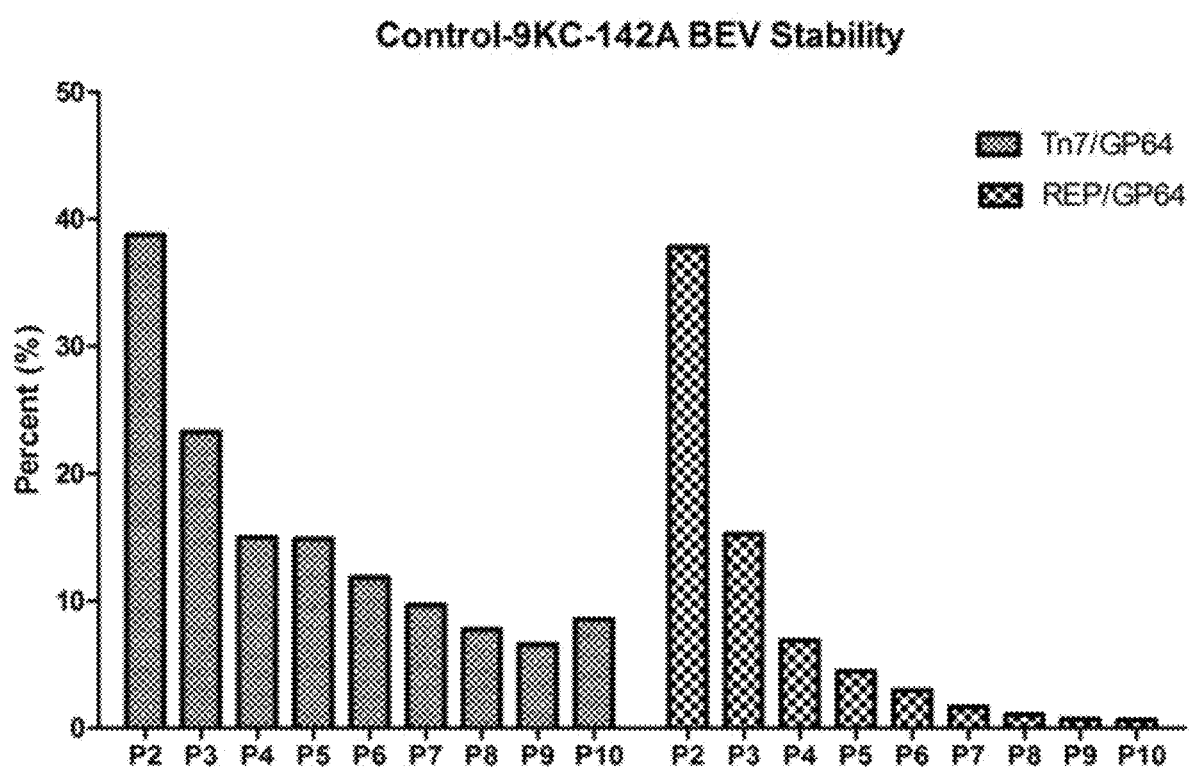
FIG. 4 shows the stability of different passages of 9KC-142A BEV according to Example 1.

FIG. 4 shows the stability of 9KC-142A BEVs in different passages in a control group. The BEV of the control group 9KC-142A was a recombinant bacmid numbered 9KC-142A, which was constructed as a control virus by referring to the method in the patent CN106544325A. The stability of BEV in passages P2-P10 was detected by Q-PCR. The percentage of Tn7/GP64 represented the stability of the ITR-GOI expression cassettes on the BEV, and the percentage of REP/GP64 represented the stability of Rep and Cap expression cassettes on the BEV. The control viruses exhibited poor stability based on the analysis of the stability results of BEV in different passages in the histogram.

Figure 5:
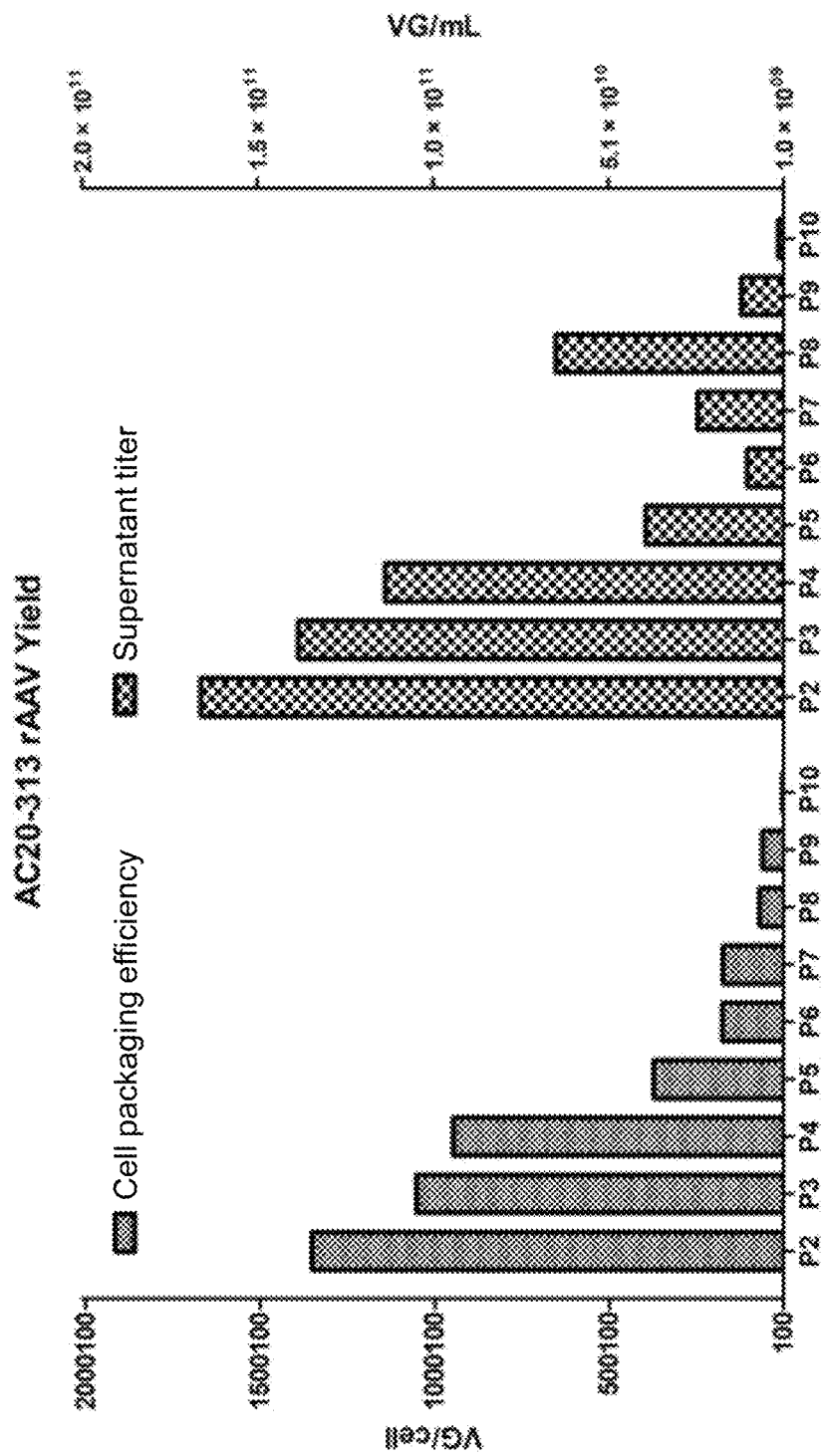
FIG. 5 shows the yields of BEV-packaged rAAV of AC20-313 in different passages as constructed according to Example 1.

FIG. 5 shows the yields of BEV-packaged rAAV of AC20-313 in different passages. The cell packaging efficiency and supernatant titer of rAAV in passages P2-P10 were detected by Q-PCR. From the histogram, it could be seen that the packaging efficiency and supernatant titer of the rAAV produced from the BEVs in the passages P2-P4 were higher; the packaging efficiency begun decreasing from P5, but the packaging efficiency still remained at 6.06E+4 vg/cell at P9, where the supernatant titer was 1.20E+10 vg/ml.

Figure 6:
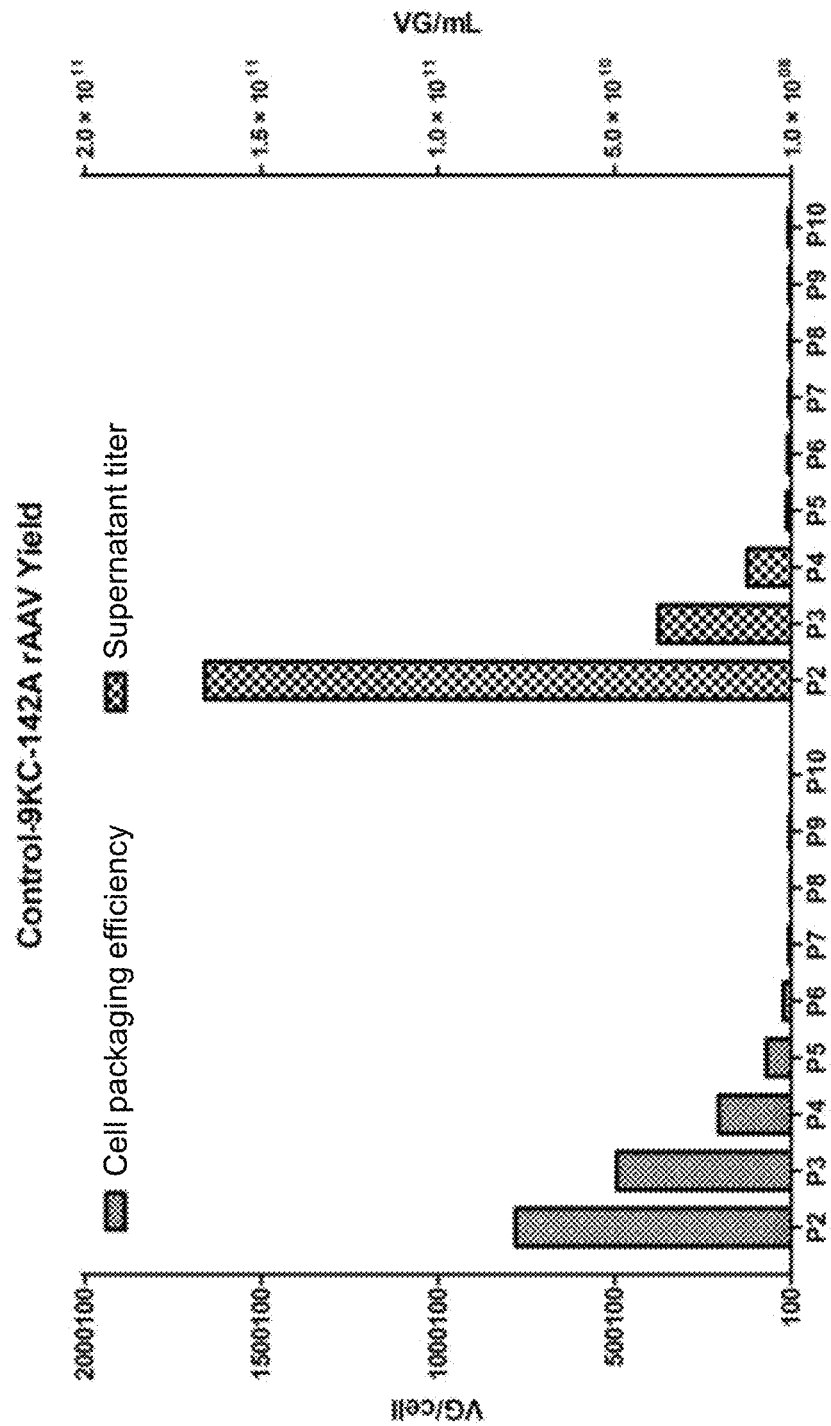
FIG. 6 shows the yields of BEV-packaged rAAV of 9KC-142A in different passages as constructed according to Example 1.

FIG. 6 shows the yields of BEV-packaged rAAV of 9KC-142A in different passages. The cell packaging efficiency and supernatant titer of rAAV in passages P2-P10 were detected by Q-PCR. From the histogram, it could be seen that the packaging efficiency significantly decreased in passages P2-P5, and the packaging efficiency at P5 was only 7.02E+4 vg/cell, with the supernatant titer of only 1.26E+9 vg/ml.

Figure 7:
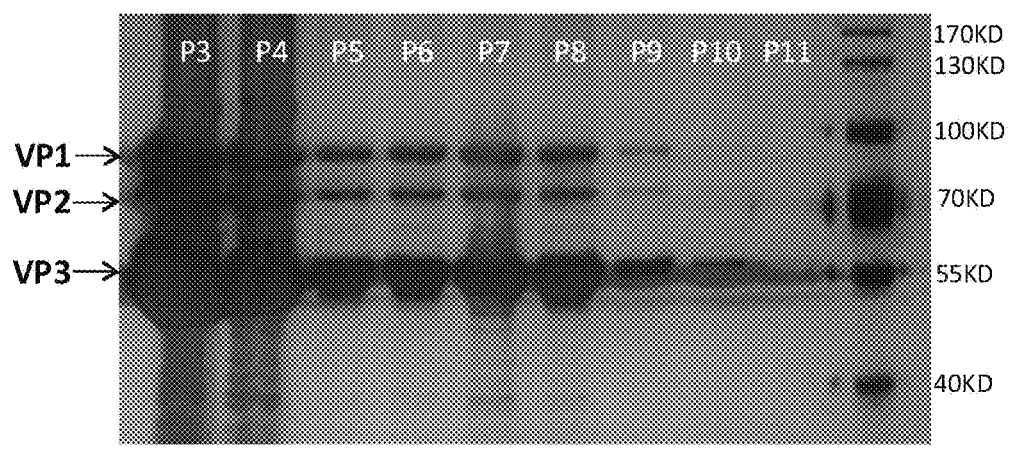
FIG. 7 shows an SDS-PAGE silver staining image of BEV-packaged rAAV of AC20-313 in passages P2-P10 as constructed according to Example 1.

FIG. 7 shows an SDS-PAGE silver staining image of BEV-packaged rAAV of AC20-313 in passages P2-P10. Three bands in the image were respectively VP1, VP2, and VP3 of AAV virus, with the sizes being 87 KDa, 72 KDa, and 62 KDa, respectively. The rAAV produced from the seed virus BEV in passage P2 was labeled as P3, and so on.

Experimental results showed that, compared with the control group 9KC 142A, the passage stability of the BEV obtained by placing the Rep/Cap expression cassettes of rAAV at the 2625 bp of the C-terminal of the essential gene Ac135 gene in this example was significantly enhanced, as shown in FIG. 3. Specifically, the percentage of Tn7/GP64 remained constant without decrease, and the percentage of REP/GP64 decreased slowly, which was decreased by about 2.4-fold by comparing P10 (26.72%) with P2 (64.97%). For the control group 9KC 142A, the percentages of Tn7/GP64 and REP/GP64 decreased significantly, and the percentage of REP/GP64 decreased by 59-fold by comparing P10 (0.64%) with P2 (37.78%). Moreover, the percentage of REP/GP64 at P4 had decreased to 6.88% (by 5.5-fold). At the same time, the supernatant titer and cell packaging efficiency of rAAV (AC20 313) produced by infecting the host cells sf9 with BEV from different passages were also significantly better than those of the control group 9KC-142A. The packing efficiency of AC20 313 at P2/P3/P4 was basically at 1E+6 VG/Cell, and begun decreasing slowly from P5 (by 2.5-fold, with the packing efficiency of 3.72E+5 vg/cell). The packaging efficiency at P9 remained as 6.06E+4 VG/Cell, indicating that the stability of the produced rAAV was greatly improved. On the other hand, the packaging efficiency of the control group 9KC 142A decreased significantly at passages P2 P5, wherein the packaging efficiency at P5 was only 7.02E+4 vg/cell, with the supernatant titer of only 1.26E+9 vg/ml, as shown in FIG. 6.

200 ml of sf9 cells were respectively infected at the same MOI with the prepared BEV in passages P2, P3, P4, P5, . . . , and P10 passages in this example. The cell activity was detected 3 days after infection, and the activity was lower than 50%. The cells were centrifuged to respectively harvest cell pellets and supernatant, and the harvested cell pellets and supernatant were respectively purified. The cells were lysed by repeated freezing and thawing three times, and then centrifuged at 5000 rpm for 10 min to collect supernatant. Nuclease (Benzonase) was added to the supernatant and treated in a water bath at 37° C. for 60 min. After treatment, the supernatant was centrifuged at 5000 rpm for 10 min. The collected cell lysate and collected supernatant were precipitated with PEG and resuspended, and then separated and purified by iodixanol density gradient centrifugation (refer to Aslanidi et al., 2009, Proc. Natl Acad. Sci. USA, 206: 5059-5064 for a method). The finally-purified finished product virus was all resuspended in 185 ul of PBS, and 10 ul of the purified finished product virus in each passage was treated in SDS-PAGE gel for silver staining. The results are as shown in FIG. 7.

P3, P4, . . . , and P11 labeled in the gel image represented the rAAV produced by amplification with the seed virus BEV of the previous passage. As can be seen from FIG. 7, when the rAAV virus package was performed with different passages of BEV (P2-P10), the seed viruses BEV at P2-P7 showed better stability, with a slight decrease in the total amount of the produced rAAV. This was consistent with the results in FIG. 3. The rAAV in the lanes P3 and P4 showed very high virus concentration, resulting in darker lanes. When rAAV were amplified with seed viruses representing BEV in P2 and P3, the packaging efficiency of the viruses was very high.

Therefore, the Rep and Cap expression cassettes were placed next to the site of the essential gene AC135 of baculovirus, and the ITR GOI expression cassette was still placed at the locus of the non-essential gene Polh by Tn7 recombination, in order to improve the passage stability of BEV and the ability to produce rAAV stably.

Example 2

In Example 1, by targeting the capsid protein gene expression cassette (Cap) and Rep gene expression cassette (Rep) of rAAV to the essential gene Ac135 gene, the prepared recombinant baculovirus bacmid had the BEV stability and rAAV packaging efficiency higher than those prepared by placing the Rep/Cap on the locus of the non-essential gene PH. In view of this, in the following example, Rep/Cap was placed next to the essential gene GP64, and the core expression element ITR-GOI expression cassette of rAAV was placed at the C-termini of various essential genes of baculovirus, in order to evaluate the stability of BEV and the packaging efficiency of rAAV.

rAAV were prepared by using DH10Bac-ΔCC-Cap-Rep (GP64)-ITR-GOI(Ac135).

This example included two homologous recombinant vectors. One homologous recombinant vector, targeted an essential gene GP64, contained Cap and Rep expression cassette of functional protein components essential for producing the rAAV, a Chol expression cassette and an ETL-EGFP expression cassette, wherein the Chol expression cassette served as a positive clone selection marker for Red homologous recombination, and the ETL-EGFP expression cassette was used for TCID50 titration of BEV. The other homologous recombinant vector, targeting an essential gene Ac135 gene, contained an expression cassette of a core expression element ITR-GOI of the rAAV and a Gen expression cassette.

With the preparation system for the rAAV in this example, the preparation method for the rAAV included the following steps.

2.1 A homologous recombinant vector which contained the capsid protein gene expression cassette (Cap) and Rep gene expression cassette (Rep) of rAAV and targeted the essential gene GP64 gene and a homologous recombinant vector which contained ITR GOI and targeted the essential gene Ac135 gene were constructed, respectively.

2.1.1 A homologous recombinant vector which contains the capsid protein gene expression cassette (Cap) and Rep gene expression cassette (Rep) of rAAV and targeted GP64 gene was constructed. Three genes Chia, Cath and GP64 in the wild-type AcMNPV genome were adjacent to each other. In a preferred solution used in this example, the capsid protein gene expression cassette (Cap) and Rep gene expression cassette (Rep) of rAAV were inserted into the C-terminal of GP64, and the genes Chia and Cath were deleted at the same time. First, with a wild-type AcMNPV bacmid DNA as a template, an upstream homologous arm fragment HAL(GP64) (SEQ ID No. 8) was amplified by using primers (HAL(GP64) F: ggtaacggccaattcaacgt and HAL(GP64) R: aagcaatatattgagtatca), and a downstream homologous arm fragment HAR(GP64) (SEQ ID No. 9) was amplified by using primers (HAR(GP64) F: tctcaacacactcgctatttgga and HAR(GP64) R: tggagaacaccaagtttggcggcgt).

Then, DNA fragments, including the upstream homologous arm, the downstream homologous arm, a chloramphenicol resistance gene expression cassette (P1-FRT-Chlo-P2), a Cap9 gene expression cassette (P10-Cap9-PA), and a Rep2 gene expression cassette (PH-Cap9-PA), were cloned together into a pUC57 vector to obtain a homologous recombinant vector pUC57-HAL(GP64)-P1-FRT-Chol-P2-ETLEGFP-PA-Cap9KC-Rep2-HAR(GP64) targeting the GP64 gene.

2.1.2 A homologous recombinant vector containing the ITR core element (ITR-GOI) and targeting the Ac135 gene was constructed. In this example, the ITR core expression element used a red fluorescent protein (mcherry) expression cassette. The expression of mcherry was controlled by a miniEfla promoter, which is convenient for detecting the activity of rAAV. First, with a wild-type AcMNPV bacmid DNA as a template, primers were designed to amplify an upstream homologous arm fragment HAL (Ac135) (SEQ ID No. 6) and a downstream homologous arm fragment HAR (Ac135) (SEQ ID No. 7).

Then, the upstream homologous arm, the downstream homologous arm, a gentamicin resistance gene expression cassette (P1 FRT Chlo P2), and an ITR core element gene expression cassette (ITR GOI) were cloned together onto a vector pUC57, to obtain a homologous recombinant vector pUC57 HAL(Ac135) P1 FRT Gen P2 Tn7L ITR miniEF1a mcherry WPRE PA I TR HAR(Ac135), which targeted the Ac135 gene and carried the ITR GOI.

2.2 The capsid protein gene expression cassette (Cap) and Rep gene expression cassette (Rep) of the rAAV and the ITR core element (ITR-GOI) containing an exogenous gene of interest (GOI) were respectively inserted into the C-terminal of the essential gene GP64 gene and the C-terminal of the essential gene Ac135 gene in the baculovirus genome, to obtain a recombinant bacmid containing the recombinant baculoviral genome with the functional protein components essential for producing the rAAV and the ITR core element.

2.2.1 Referring to Step 1.1.4 in Example 1, the capsid protein gene expression cassette (Cap) and Rep gene expression cassette (Rep) of the rAAV were inserted into the C-terminal of the essential gene GP64 gene in the baculovirus genome, and positive strains were selected and named DH10Bac ΔCC Cap9 Rep2(GP64).

2.2.2 Then, referring to Step 1.1.4 in Example 1, the ITR core element (ITR-GOI) containing the exogenous gene of interest (GOI) was inserted into the C-terminal of the essential gene Ac135 gene in the recombinant baculoviral genome obtained from 2.2.1; and positive monoclonal strains were selected and named DH10Bac ACC Cap Rep (GP64) ITR GOI(Ac135). Bacmids were extracted to obtain recombinant bacmids numbered Ac-141-175, which contained the recombinant baculoviral genome with the capsid protein gene expression cassette (Cap) and Rep gene expression cassette (Rep) of rAAV and the ITR core element. The Rep and Cap expression cassettes in the bacmid were located at 235 bp at the C-terminal of the essential gene GP 64 gene of baculovirus; and the ITR core element was located at 1503 bp at the C-terminal of the essential gene Ac135 gene of baculovirus.

2.3 The recombinant bacmid Ac 141 175 containing the recombinant baculoviral genome with the functional protein components essential for producing the rAAV and the ITR core element obtained from Step 2.2 was transfected into a host cell line and cultured to obtain a recombinant baculovirus.

DNA of the recombinant bacmid were extracted and transfected into Sf9 insect cells to prepare recombinant baculovirus BEV and rAAV. The transfected St9 insect cells successfully produced BEV, and BEV were replicated and proliferated in large numbers for further infection, leading to obvious cytopathic effects (CPE) in St9 cells. The apparent expressions of green fluorescent proteins (GFP) and red fluorescent proteins could be observed under the fluorescence microscope. The culture supernatant of Sf9 cells with CPE was collected, which contained a large amount of BEV, i.e., the 0th passage of BEV (P0); and Sf9 cells containing a large amount of rAAV were collected at the same time. Sf9 cells cultured in suspension were infected with the prepared BEV-P0s at a multiplicity of infection (MOI) of 3. After 72 hours of infection, the cell activity decreased to below 50%. The cell culture solution was centrifuged at 1000 g for 5 min, and the culture supernatant and cell pellets were collected respectively. The supernatant was labeled as the first passage of BEV-P1, and the cells were labeled as BEV-P0-packaged rAAV.

The stability of the recombinant baculoviruses produced in this system and the yield stability of AAVs were teste.

The contrast baculovirus was a recombinant baculovirus numbered 9KC 313(ITR miniEfla mcherry WPRE PA ITR), which was obtained by referring to the method in the patent CN109609552B. 9KC 313 was prepared by the following steps: inserting the capsid protein gene expression cassette (Cap9) and Rep gene expression cassette (Rep) of rAAV into the loci of non-essential genes (Cath and Chia); then inserting the ITR GOI into a locus of the non-essential gene Polh by Tn7 recombination to obtain a recombinant bacmid containing the recombinant baculovirus genome; and finally transfecting Std cells to obtain the recombinant baculovirus.

In order to further analyze the stability of the system in this example, the BEV-Cap-Rep(GP64)-ITR-GOI(Ac135) prepared in this example was serially passaged at the same MOI to infect the Sf9 cells, so as to obtain BEV of passages P2, P3, P4, P5, . . . , and P10. The passage stability of the recombinant baculoviruses was tested.

The titers of BEV in all the passages were measured by using the quantitative PCR (qPCR) method, and the titer unit was VG/ml (VG, virus genomes). The total baculovirus titers were measured by using a pair of primers (Q GP64 F: AACTTGGACATTACCCCGCC and Q GP64 R: CCGTTGTACGCATACGCCTG) corresponding to the gp64 gene; the titers of the baculoviruses containing the Rep and Cap expression cassettes were measured by using a pair of qPCR primers (Q Rep F: GAACAAGGTGGTGGACGAGT and Q Rep R: ATTCAAACAGGCGCTTAAAT) corresponding to the Rep sequence; and the titers of the baculoviruses containing the ITR GOI were measured by using a pair of primers (Q Tn7 F: tcgtattagcttacgacgctaca and Q Tn7 R: tagttgggaactgggagggg) corresponding to the Tn7 sequence. Based on the ratios of Tn7/GP64 and REP/GP64, the passage stability of the exogenous gene fragments (the Rep/Cap expression cassettes and the ITR-GOI expression cassette) in the BEV was evaluated. If the ratios were constant, it indicated good passage stability of the Rep/Cap expression cassettes and the ITR-GOI expression cassette. If the ratios decreased significantly with the increase of the number of passages, it indicated poor stability of the inserted exogenous fragments. The passage of multiplicity of infection (MOI) was calculated by using the total BEV titer, i.e., the Q-PCR titer of GP64, throughout the passaging process.

In another aspect, evaluating the passage stability of the recombinant baculovirus involved the packaging efficiency and supernatant titer of the recombinant adeno-associated virus (rAAV). The titers of rAAV in all passages were measured by qPCR method, and the titer unit was VG/ml (VG, virus genomes). The titers of rAAVs were detected by using a pair of primers (Q WPRE F:CCGTTGTCAGGCAACGTG and QWPRE R:AGCTGACAGGTGGTGGCAAT) targeting the WPRE sequence. The detection results are as shown in FIG. 8 to FIG. 12.

Figure 8:
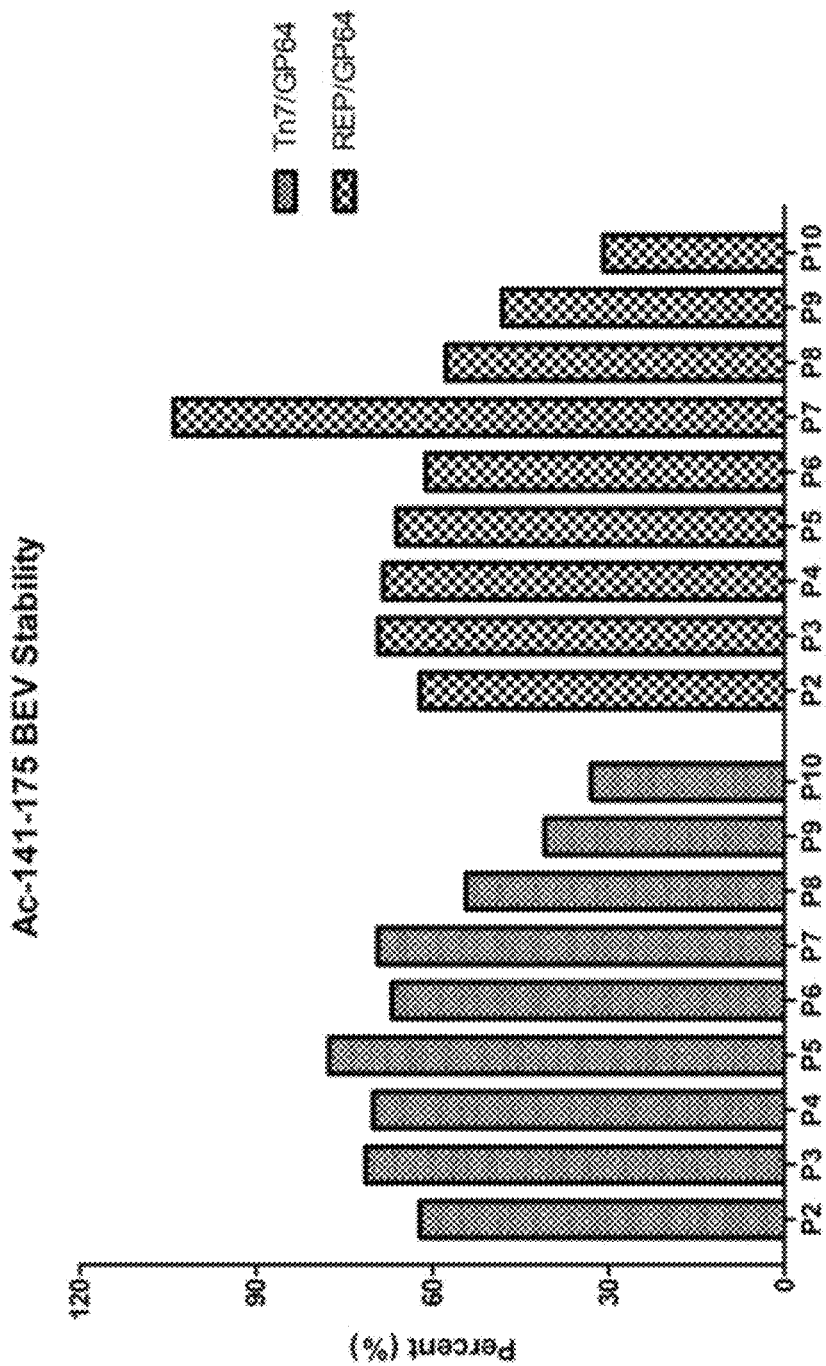
FIG. 8 shows the stability of Ac-141-175 BEV in different passages according to Example 2.

FIG. 8 shows the stability of Ac-141-175 BEVs in different passages. The Rep and Cap expression cassettes of rAAV were placed at the C-terminal of the essential gene GP64 of baculovirus, and the ITR GOI expression cassette of rAAV was placed at the C-terminal of the essential gene Ac135 of baculovirus. The bacmid was numbered Ac 141 175. The stability of BEV in passages P2-P10 was detected by Q-PCR. Good stability was shown based on the analysis of the stability results of BEV in different passages in the histogram.

Figure 9:
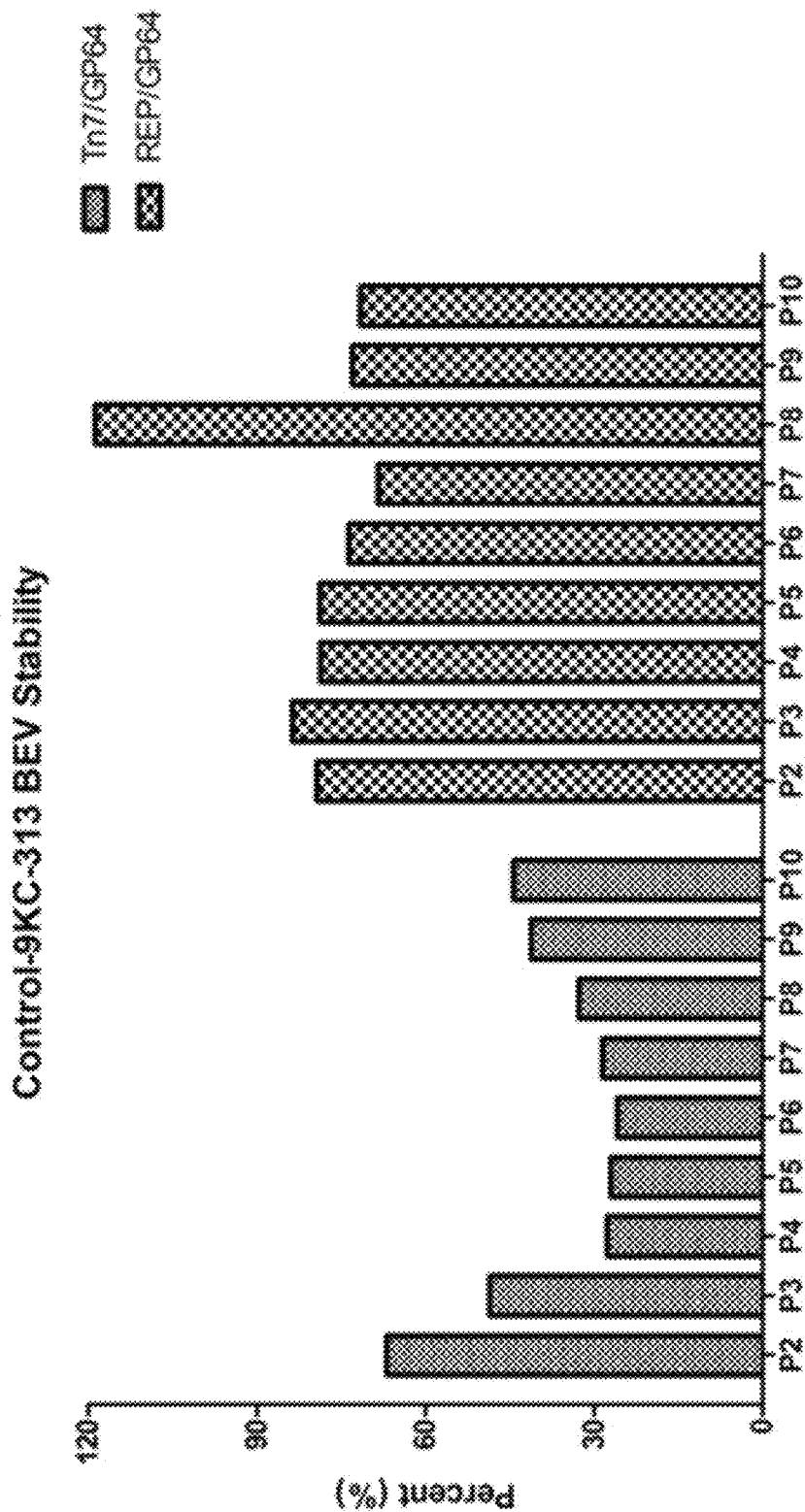
FIG. 9 shows the stability of 9KC-313 BEV in different passages according to Example 2.

FIG. 9 shows the stability of control group 9KC 313 BEV in different passages. The BEV of the control group 9KC 313 was a recombinant bacmid numbered 9KC 313, which was constructed as a control virus by referring to the method in the patent CN109609552A. The stability of BEV in passages P2-P10 was detected by Q-PCR. From the analysis of the stability results of BEV in different passages in the histogram, the ratio of Tn7/GP64 was slightly low, and decreased to 27.66% at passage P4.

Figure 10:
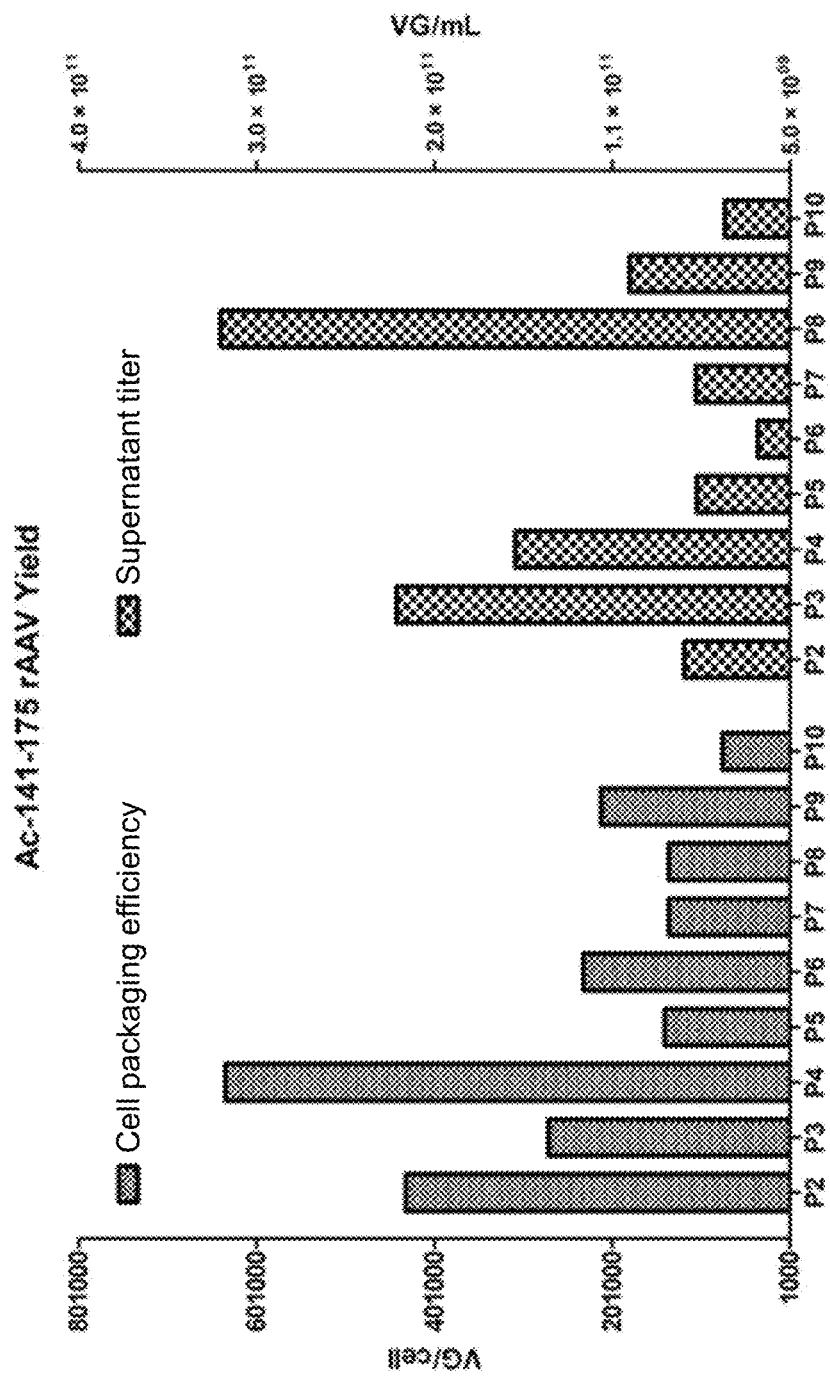
FIG. 10 shows the yields of BEV-packaged rAAV of Ac-141-175 in different passages according to Example 2.

FIG. 10 shows the yields of BEV-packaged rAAV of Ac-141-175 in different passages. The cell packaging efficiency and supernatant titer of rAAV in passages P2-P10 were detected by Q-PCR. From the histogram, it could be seen that the packaging efficiency and the supernatant titer were both stable. At passage P9, the packaging efficiency still remained at 2.14E+5 vg/cell, and the supernatant titer reached 9.12E+10vg/ml.

Figure 11:
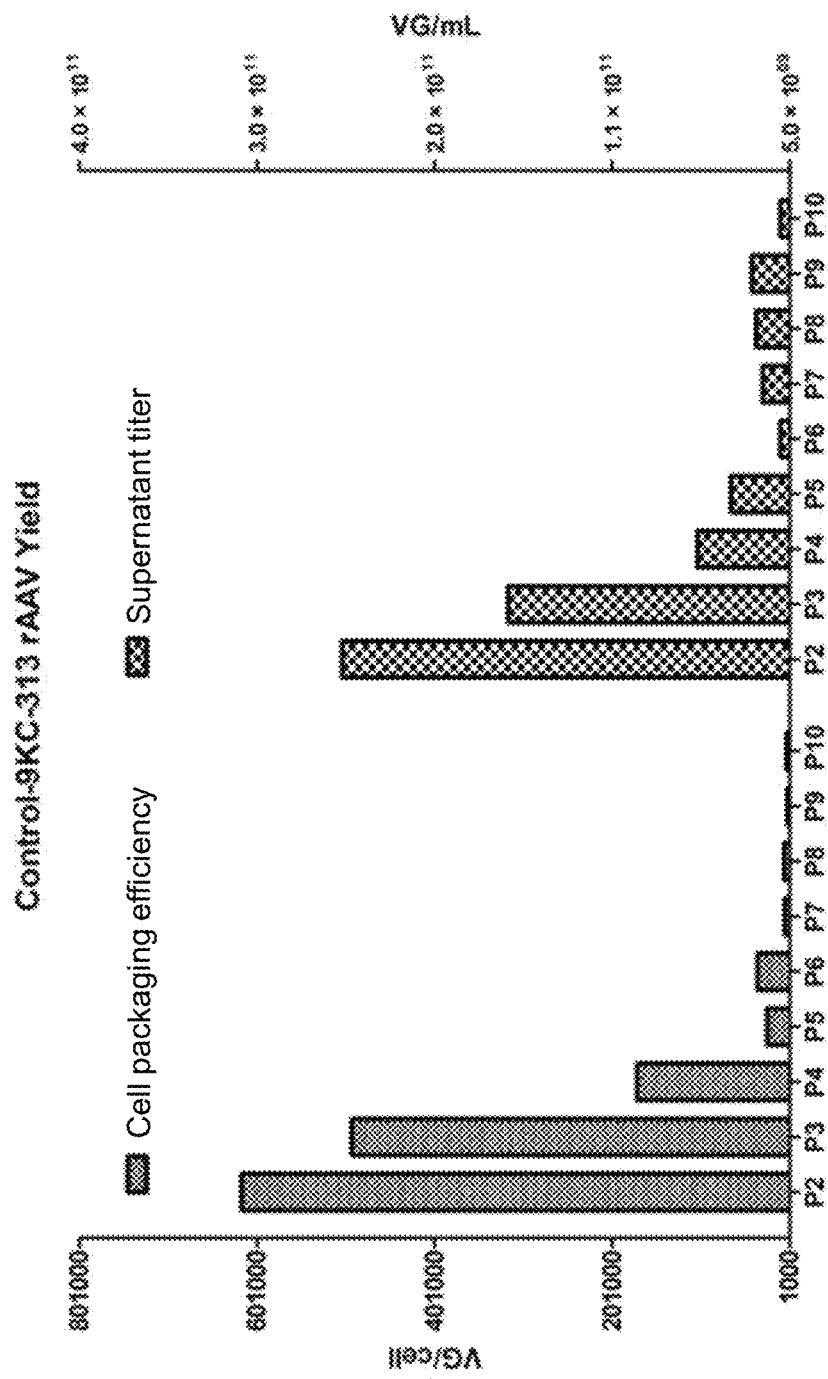
FIG. 11 shows the yields of BEV-packaged rAAV of 9KC-313 in different passages according to Example 2.

FIG. 11 shows the yields of BEV-packaged rAAV of the control group 9KC 313 in different passages. The cell packaging efficiency and supernatant titer of rAAV in passages P2-P10 were detected by Q-PCR. From the histogram, it could be seen that the rAAV produced from BEV of the control viruses in different passages showed poor stability, and the packaging efficiency significantly decreased, which was only 2.62E+4vg/cell at passage P5.

Figure 12:
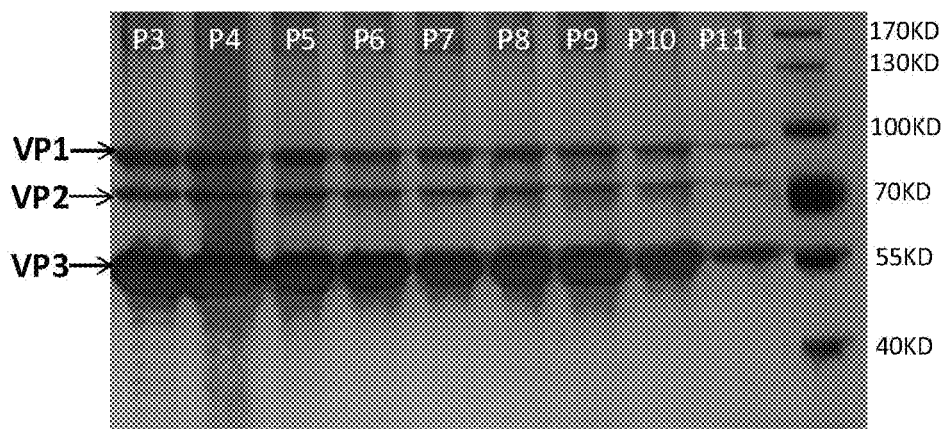
FIG. 12 is an SDS-PAGE silver staining image of BEV-packaged rAAV of Ac-141-175 in passages P2 P10 according to Example 2.

FIG. 12 is an SDS-PAGE silver staining image of BEV-packaged rAAV of Ac-141-175 in passages P2 P10. Three bands in the image were respectively VP1, VP2, and VP3 of AAV virus, with the sizes being 87 KDa, 72 KDa, and 62 KDa, respectively. The rAAV produced from the seed virus BEV in passage P2 was labeled as P3, and so on.

Experimental results showed that, compared with the control group 9KC 313, the passage stability of the BEV obtained by placing the Rep/Cap expression cassettes of rAAV at the 235 bp of the C-terminal of the essential gene GP64 gene and placing the ITR-GOI expression cassette at 2625 bp at the C-terminal of the essential gene Ac135 gene of baculovirus was significantly enhanced in this example (FIG. 8). Specifically, the percentages of Tn7/GP64 and REP/GP64 remained constant without decrease at P2-P7. The percentage of Tn7/GP64 decreased by about 1.9-fold by comparing P10 (33.00%) with P2(62.08%). For the control group 9KC-313, the percentage of Tn7/GP64 decreased by 2.4-fold from 66.92% at P2 to 27.66% at P4. The ratio of Tn7/GP64 reflected the stability of ITR-GOI. The results of the packaging efficiency of rAAV (FIG. 9, FIG. 10) further indicated that the BEV of the Ac-141-175 in passages P2-P9 could have the packaging efficiency of 1E+5 VG/cell, and the cell packaging efficiency of BEV of control group 9KC-313 in different passages decreased rapidly, from 4.94E+5 VG/cell at P3 to 1.73E+5 VG/cell at P4 and 2.62E+4 VG/cell at P5.

200 ml of sf9 cells were respectively infected at the same MOI with the prepared BEV in passages P2, P3, P4, P5, . . . , and P10 passages in this example. The cell activity was detected 3 days after infection, and the activity was lower than 50%. The cells were centrifuged to harvest cell pellets and supernatant respectively, and the harvested cell pellets and supernatant were respectively purified. The cells were lysed by repeated freezing and thawing three times, and then centrifuged at 5000 rpm for 10 min to collect supernatant. Nuclease (Benzonase) was added to the supernatant and treated in a water bath at 37° C. for 60 min. After treatment, the supernatant was centrifuged at 5000 rpm for 10 min. The collected cell lysate and collected supernatant were precipitated with PEG and resuspended, and then separated and purified by iodixanol density gradient centrifugation (refer to Aslanidi et al., 2009, Proc. Natl Acad. Sci. USA, 206: 5059 5064 for a method). The finally-purified finished product virus was all resuspended in 185 ul of PBS, and 10 ul of the purified finished product virus in each passage was treated in SDS-PAGE gel for silver staining. The results are as shown in FIG. 12.

As can be seen from FIG. 12, when the rAAV virus packaging was performed with different passages of BEV (P2-P10), the seed viruses BEV at P2-P9 showed better stability, with a slight decrease in the total amount of the produced rAAV. This was consistent with the results in FIG. 10.

Therefore, placing the ITR GOI next to the position of the essential gene AC135 of baculovirus improved the passage stability of BEV and the ability of BEV to stably produce rAAV, showing great significance for large-scale production of rAAV.

Example 3

The Rep/Cap expression cassettes of rAAV was immobilized at 235 bp at the C-terminal of the essential gene GP64 gene of baculovirus, and the loci of other essential genes of baculovirus were tested continuously, and rAAV was prepared by using DH10Bac ACC Cap Rep(GP64) ITR GOI (38K).

Referring to the step in Example 2.1, an upstream homologous arm HAL(38K) (SEQ ID No. 10) was amplified by using primers (HAL(38K) F: tcggcgaacgtgttttgtcccaa and HAL(38K) R: ctattcattgtcgctgtcttct), a downstream homologous arm HAR(38K) (SEQ ID No. 11) was amplified by using primers (HAR(38K) F: agtttatatttttatttaata and HAR (38K) R: gatcatgtagcacactcgatgcga), and a homologous recombinant vector containing the ITR core expression element (ITR GOI) and targeting an essential gene 38K gene in the baculoviral genome was constructed. Then, referring to Step 1.1.4 in Example 1, the ITR-GOI was inserted at 126 bp at the C-terminal of the essential gene 38K gene in the recombinant baculoviral genome obtained from 2.2.1, and positive monoclonal strains were selected and named DH10Bac ΔCC Cap Rep(GP64) ITR GOI(38K). The bacmid was extracted to obtain a recombinant bacmid numbered Ac 141 163, which contained the recombinant baculoviral genome with the capsid protein gene expression cassette (Cap), Rep gene expression cassette (Rep) and ITR core element for producing the rAAV.

Figure 13:
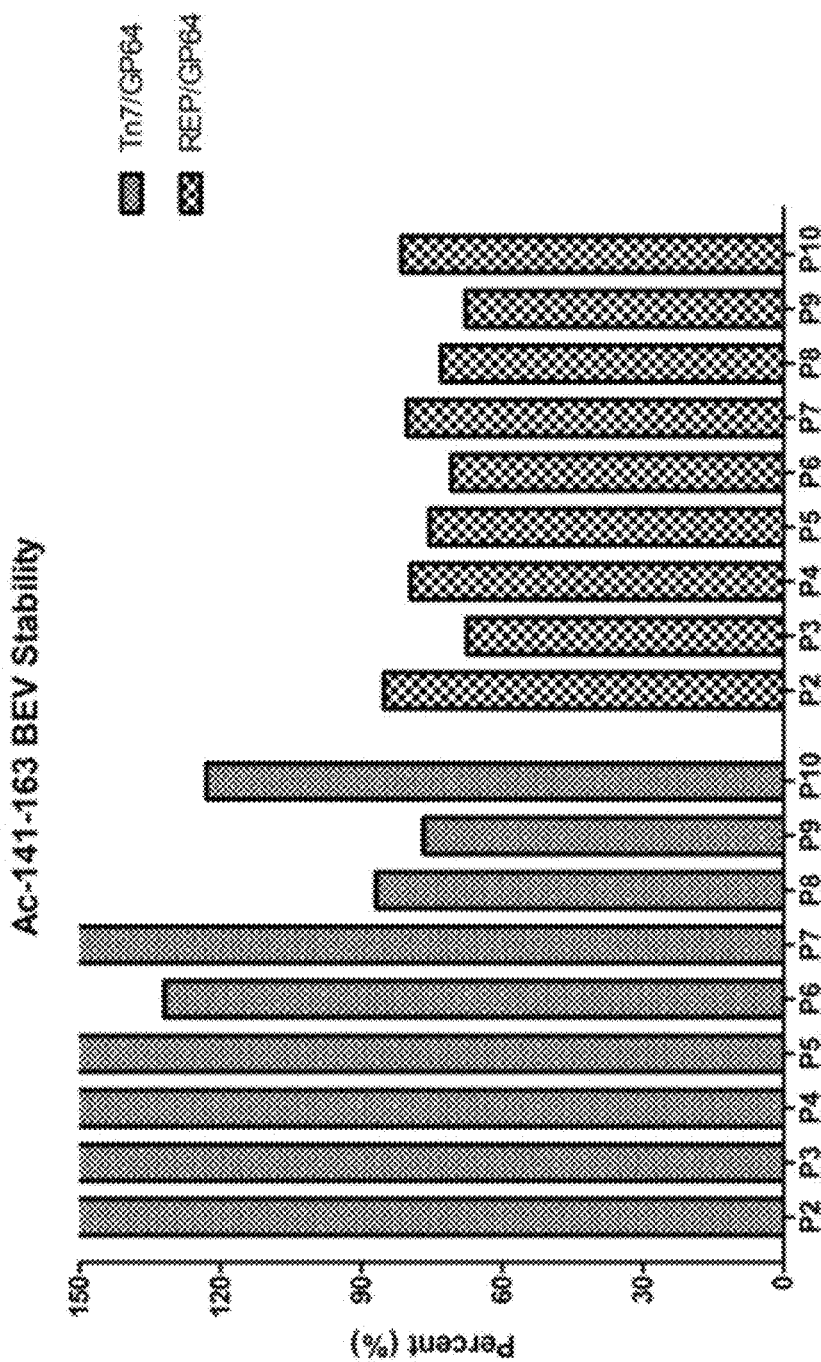
FIG. 13 shows the stability of Ac-141-163 BEV in different passages according to Example 3.
Figure 14:
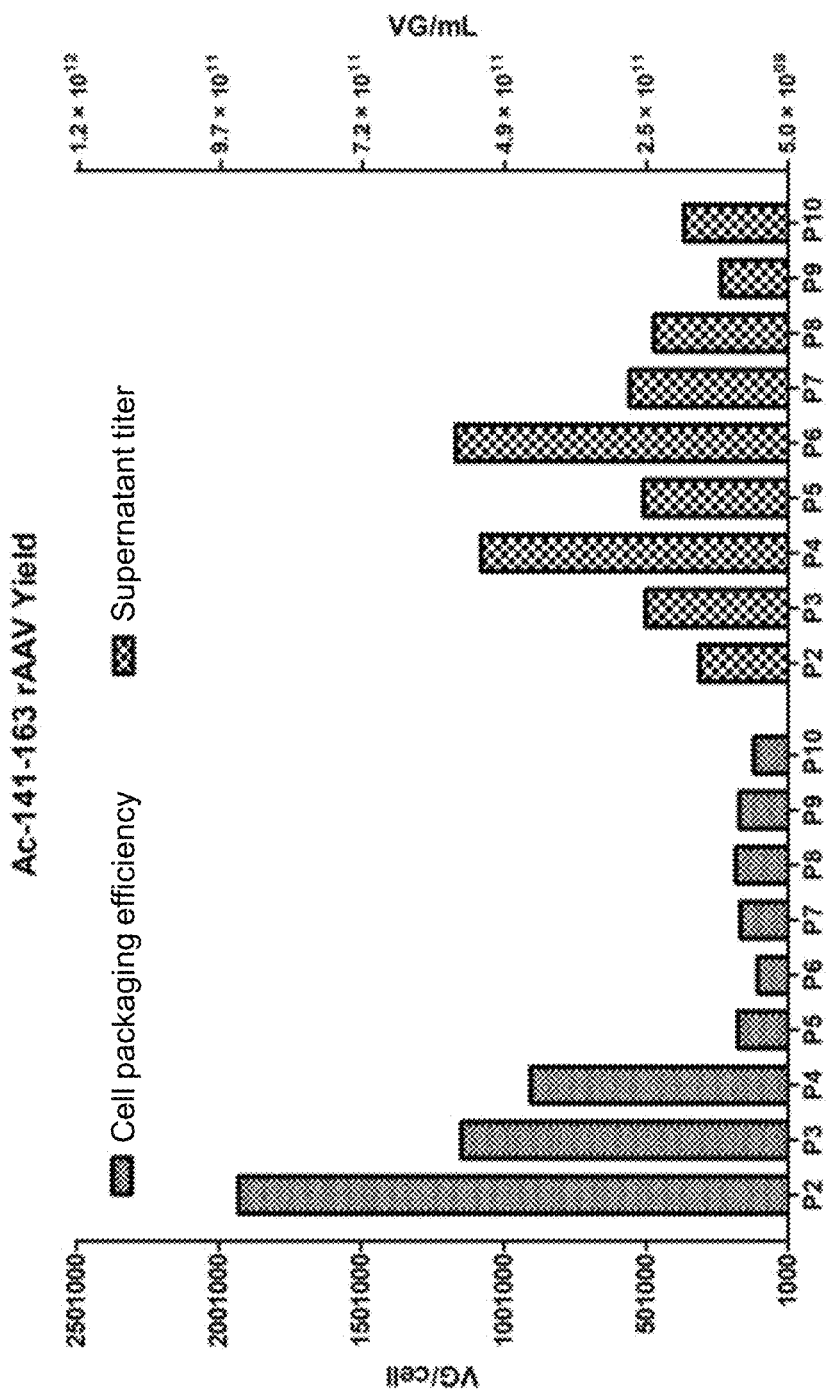
FIG. 14 shows the yields of BEV-packaged rAAV of Ac-141-163 in different passages according to Example 3.
Figure 15:
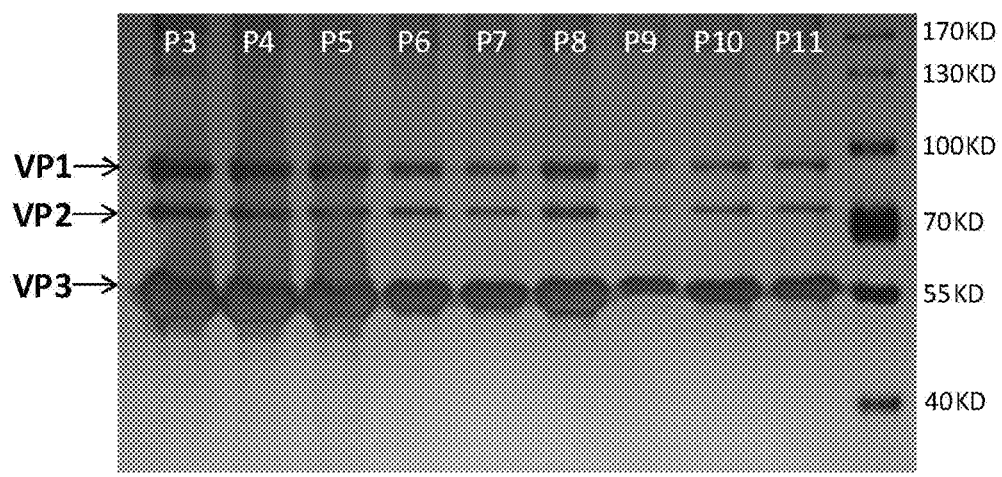
FIG. 15 is an SDS-PAGE silver staining image of BEV-packaged rAAV of Ac-141-163 in passages P2-P10 according to Example 3.

The passage stability test for BEV was carried out according to the method in Example 2, and the test data were shown as in FIG. 13, FIG. 14 and FIG. 15.

FIG. 13 schematically shows the stability of Ac 141 163 BEV in different passages. The ITR-GOI expression cassette of rAAV was placed at 126 bp of the C-terminal of the essential gene 38K of baculovirus, and the bacmid was numbered Ac-141-163. The stability of BEVs in passages P2-P10 was detected by Q-PCR. Good stability was shown based on the analysis of the stability results of BEV in different passages in the histogram.

FIG. 14 schematically shows the yields of BEV-packaged rAAV of Ac 141 163 in different passages. The cell packaging efficiency and supernatant titer of rAAV in passages P2-P10 were detected by Q-PCR. From the histogram, it could be seen that the packaging efficiency begun to decrease at passage P5, but the packaging efficiency at passage P10 still remained at a high level of 1.21E+5 vg/cell, with the supernatant titer here reached 1.84E+11 vg/ml.

FIG. 15 is an SDS-PAGE silver staining image of BEV-packaged rAAV of Ac-141-163 in passages P2-P10. Three bands in the image were respectively VP1, VP2, and VP3 of AAV virus, with the sizes being 87 KDa, 72 KDa, and 62 KDa, respectively. The rAAV produced from the seed virus BEV in passage P2 was labeled as P3, and so on.

From the above results, it could be seen that, compared with the control virus 9KC-313 in Example 2, the percentages of Tn7/GP64 and Rep/GP64 of BEVs of Ac-141-163 in different passages were very stable. The packaging efficiency and supernatant titer of its rAAV remained at a high level. The packing efficiencies at P2-P4 remained at 1.00E+6 VG/cell. Although the packing efficiency decreased from 9.06E+5 VG/cell at P4 to 1.77E+5 VG/cell at P5, the subsequent packing efficiency remained stable until P10 at which the packing efficiency was 1.21E+5 VG/cell. In the control group 9KC-313, the packaging efficiency at P5 had decreased to 2.62E+4 VG/cell. The supernatant titer of rAAV was also maintained at a high level, reaching 5.86E+11 VG/mL (P6) at the highest level, which greatly increased the total amount of rAAV.

200 ml of sf9 cells were respectively infected at the same MOI with the prepared BEV in passages P2, P3, P4, P5, . . . , and P10 passages in this example. The cell activity was detected 3 days after infection, and the activity was lower than 50%. The cells were centrifuged to harvest cell pellets and supernatant respectively, and the harvested cell pellets and supernatant were respectively purified. The cells were lysed by repeated freezing and thawing three times, and then centrifuged at 5000 rpm for 10 min to collect supernatant. Nuclease (Benzonase) was added to the supernatant and treated in a water bath at 37° C. for 60 min. After treatment, the supernatant was centrifuged at 5000 rpm for 10 min. The collected cell lysate and collected supernatant were precipitated with PEG and resuspended, and then separated and purified by iodixanol density gradient centrifugation (refer to Aslanidi et al., 2009, Proc. Natl Acad. Sci. USA, 206: 5059 5064 for a method). The finally-purified finished product virus was all resuspended in 185ul of PBS, where the volume of P10 was 185ul*1.5=277.5ul, and the sample of P9 had a little problem during purification, leading to a decrease in the final total virus amount. 10 ul of the purified finished product virus from each passage was treated on SDS-PAGE gel for silver staining. The results are as shown in FIG. 15.

As can be seen from FIG. 15, excluding P9 at which the purification process went wrong and P10 whose actual volume was 1.5 times that of other viruses, the BEV in different passages (P2 P10) showed good seed virus stability during rAAV virus packaging, with less decrease in the total amount of rAAV produced. It further indicated that placing the Rep and Cap expression cassettes at the C-terminal of the essential gene GP64 of BEV and placing the ITR GOI at the C-terminal of the essential gene 38K of BEV could greatly stabilize the production of rAAV.

Example 4

The Rep/Cap expression cassettes of rAAV was immobilized at 235 bp at the C-terminal of the essential gene GP64 gene of baculovirus, and the loci of other essential genes of baculovirus were tested continuously, and rAAV were prepared by using DH10Bac ΔCC Cap Rep(GP64) ITR GOI (IE1).

Referring to the step in Example 2.1, an upstream homologous arm HAL (IE1) (SEQ ID No. 12) was amplified by using primers (HAL(IE1) F: atcatgacaatattgcgagt and HAL(IE1) R: ttaattaaattcgaatt), a downstream homologous arm HAR(IE1) (SEQ ID No. 13) was amplified by using primers (HAR(IE1) F: ttatacatatattttgaat and HAR(IE1) R: ccgacccagattcgcctcaat), and a homologous recombinant vector containing the ITR core expression element (ITR GOI) and targeting an essential gene IE1 gene in the baculoviral genome was constructed. Then, referring to Step 1.1.4 in Example 1, the ITR-GOI was inserted at 1237 bp at the C-terminal of the essential gene IE1 gene in the recombinant baculoviral genome obtained from 2.2.1, and positive monoclonal strains were selected and named DH10Bac ΔCC Cap Rep(GP64) ITR GOI(IE1). The bacmid was extracted to obtain a recombinant bacmid numbered Ac 141 162, which contained the recombinant baculoviral genome with the capsid protein gene expression cassette (Cap), Rep gene expression cassette (Rep) and ITR core element for producing the rAAV.

Figure 16:
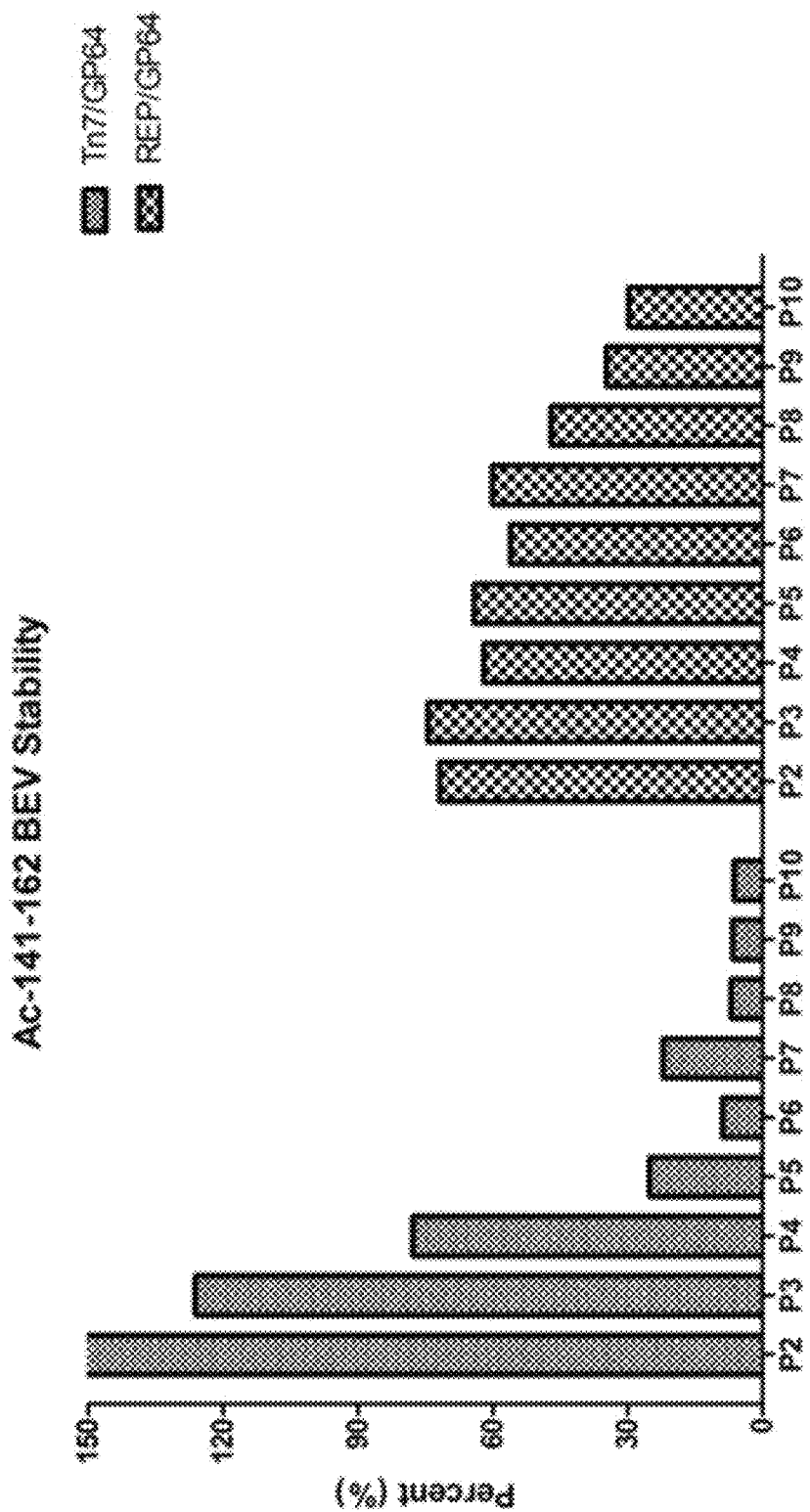
FIG. 16 shows the stability of Ac-141-162 BEV in different passages according to Example 4.
Figure 17:
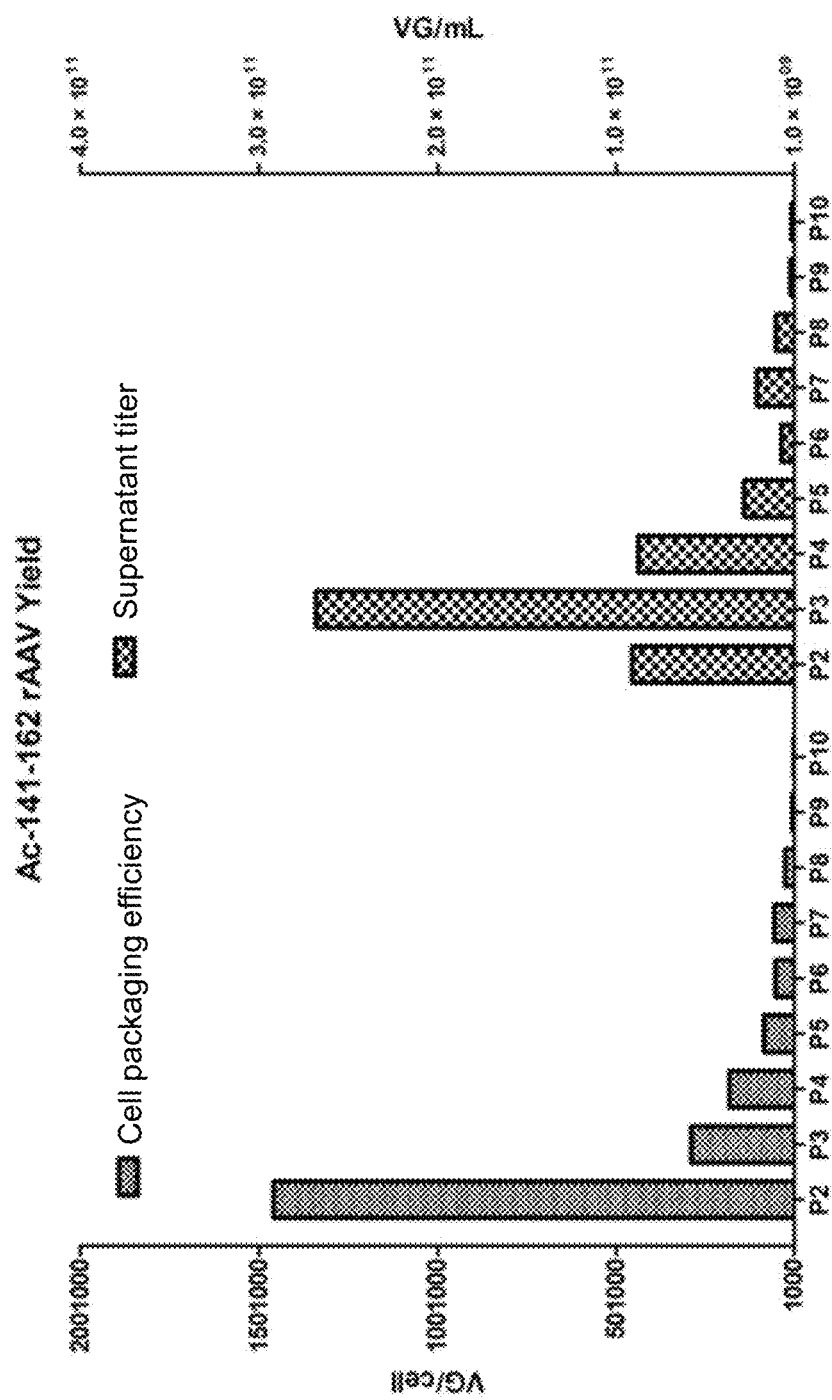
FIG. 17 shows the yields of BEV-packaged rAAV of Ac-141-162 in different passages according to Example 4.
Figure 18:
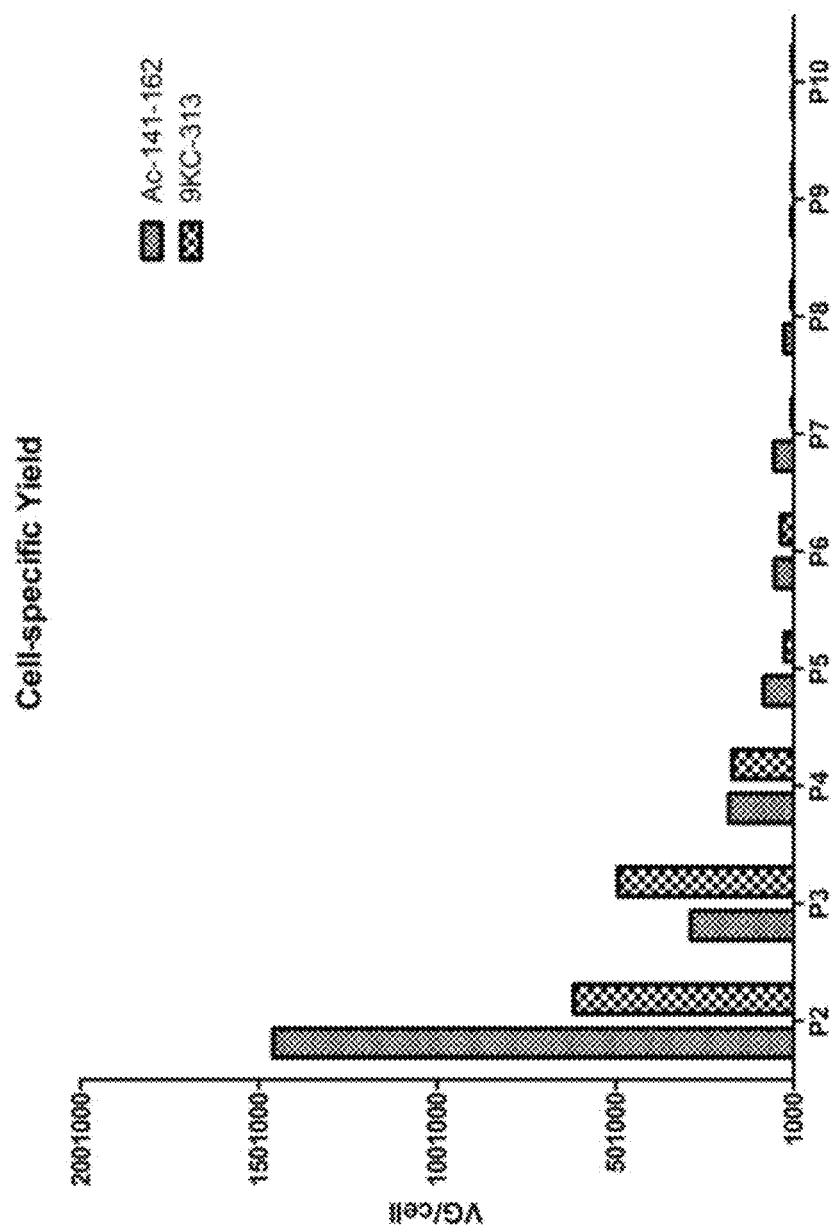
FIG. 18 shows the packing ratios of Ac-141-162 vs 9kc-313 according to Example 4.

The passage stability test for BEV was carried out according to the method in Example 2, and the test data were shown as in FIG. 16, FIG. 17 and FIG. 18.

FIG. 16 shows the stability of 16Ac 141 162 BEV in different passages. The ITR-GOI expression cassette of rAAV was placed at 1237 bp of the C-terminal of the essential gene IE1 of baculovirus, and the bacmid was numbered Ac-141-162. The stability of BEV in passages P2-P10 was detected by Q-PCR. Based on the analysis of the stability results of BEV in different passages in the histogram, the stability was similar to that of the control virus 9KC 313. FIG. 17 shows the yields of BEV-packaged rAAV of Ac-141-162 in different passages. The cell packaging efficiency and supernatant titer of rAAV in passages P2-P10 were detected by Q-PCR. From the histogram, it could be seen that the packaging efficiency decreased passage by passage, and the stability was poor.

From the above results, it could be seen that, compared with the control virus 9KC-142A in Example 1, the percentage of Rep/GP64 of BEV of Ac-141-162 in different passages was relatively stable. Similar to the control virus 9KC-313, the percentage of Tn7/GP64 of BEV of Ac-141-162 in different passages decreased rapidly, and the stability was not as good as AC20-313, Ac-141-175 and Ac-141-163 in Examples 1, 2, and 3. Tn/GP64 decreased from 165.52% at P2 to 25.18% at P5, and the packaging efficiency and supernatant titer of its rAAV also showed a gradual decrease trend. Its cell packaging efficiency and supernatant titer level were basically the same as but slightly higher than the control virus 9KC-313 (see FIG. 18). FIG. 18 shows the packing efficiency of Ac-141-162 vs 9kc-313. As can be seen from the histogram, the packaging efficiency of Ac-141-162 in each passage was slightly higher than that of the control virus 9kc-313.

Comparative Example 1

The Rep/Cap expression cassettes of rAAV was immobilized at 235 bp at the C-terminal of the essential gene GP64 gene of baculovirus, the loci of other essential genes of baculovirus were tested continuously, and rAAV was prepared by using DH10Bac ΔCC Cap Rep(GP64) ITR GOI (GP41).

Referring to the step in Example 2.1, an upstream homologous arm HAL(GP41) (SEQ ID No. 14) was amplified by using primers (HAL(GP41) F: ttttgtgaacgggctcgcta and HAL(GP41) R: tcatggcgacgactctgtaca), a downstream homologous arm HAR(GP41) (SEQ ID No. 15) was amplified by using primers (HAR(GP41) F: ttatgcagtgcgccctttcgt and HAR(GP41) R: tgccggcggcggcgattacta), and a homologous recombinant vector containing the ITR core expression element (ITR GOI) and targeting an essential gene GP41 gene in the baculoviral genome was constructed. Then, referring to Step 1.1.4 in Example 1, the ITR-GOI was inserted at 115 bp at the C-terminal of the essential gene GP41 gene in the recombinant baculoviral genome obtained from 2.2.1, and positive monoclonal strains were selected and named DH10Bac ACC Cap Rep(GP64) ITR GOI (GP41). The bacmid was extracted to obtain a recombinant bacmid numbered Ac 141 160, which contained the recombinant baculoviral genome with the capsid protein gene expression cassette (Cap), Rep gene expression cassette (Rep) and ITR core element for producing the rAAV.

In this example, the rescue and passage of BEV were carried out by referring to the method in Example 2, and the BEV rescued and passaged concurrently were numbered Ac 141 160 and Ac 141 162. The viruses with two numbers were simultaneously amplified to the passage P2. Then, 250 mL of sf9 cells were inoculated with the BEV seed virus in P2. After 3 days of infection, the cell activity was counted, and the activity was lower than 50%. The supernatant and cells were harvested respectively. The cells were lysed by repeated freezing and thawing, and then purified to pure AAV by iodixanol density gradient centrifugation. The titers of rAAV virus in the supernatant and cells during harvesting, as well as the titers and purity of the final purified rAAV were detected. Purity was detected by SDS-PAGE silver staining.

TABLE 1

| Category | Passage | Cell packaging efficiency (VG/cell) | Supernatant titer of rAAV (VG/mL) | Titer of 225 ul of finished product viruses(VG/mL) |
|---|---|---|---|---|
| Ac-141-160 | P1 | 1.60E+05 | 8.70E+10 | NA |
| | P2 | 1.34E+04 | 2.50E+10 | NA |
| | P3 | 1.69E+04 | 8.64E+10 | 2.21E+13 |
| Ac-141-162 | P1 | 1.72E+05 | 6.60E+11 | NA |
| | P2 | 2.62E+03 | 2.37E+09 | NA |
| | P3 | 2.79E+04 | 1.77E+11 | 3.15E+13 |

Figure 19:
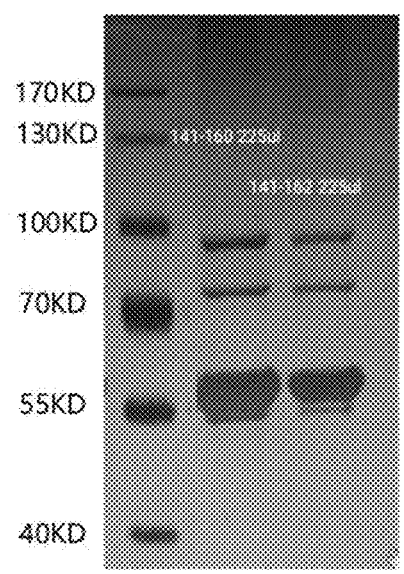
FIG. 19 is an SDS-PAGE silver staining image of rAAVs produced from Ac-141-160 and Ac-141-162 BEV.

FIG. 19 shows the SDS-PAGE silver staining image of rAAV produced from Ac-141-160 (with the ITR-GOI expression cassette of rAAV placed at the C-terminal of the essential gene GP41 of baculovirus) and Ac-141-162 BEV. When the titers of the two viruses detected by Q-PCR were the same, VP3 of Ac-141-160 was thicker, indicating a high empty capsid rate. Combining the results in Table 1 and FIG. 19, it could be seen that the titer of the finished product viruses produced from Ac-141-162 in P3 was 3.15E+13 VG/mL, and the titer of the finished product virus produced from Ac-141-160 in P3 was 2.21E+13 VG/mL. However, the VP3 band of Ac-141-160 in SDS-PAGE was obviously thicker, indicating that the rAAV produced from Ac-141-160 had an empty capsid rate higher than that of Ac-141-162. Based on analysis, the reason may lie in that placing the ITR-GOI at the C-terminal of the essential gene GP41 gene (equivalent to placing it in front of a start codon at the N-terminal of the Ac79 gene) may affect the expression of the Ac79 gene, which affects the proliferation of the baculovirus. Therefore, placing the ITR-GOI expression cassette at the C-terminal of the essential gene GP41 may not be the optimal choice.

Comparative Example 2

The Rep/Cap expression cassettes of rAAV was immobilized at 235 bp at the C-terminal of the essential gene GP64 gene of baculovirus, the loci of other essential genes of baculovirus were tested continuously, and rAAV was prepared by using DH10Bac ACC Ca p Rep (GP64) ITR GOI(Ac153).

Referring to the step in Example 2.1, an upstream homologous arm HAL (Ac153) (SEQ ID No. 16) was amplified by using primers (HAL(Ac153) F: tgacataaatatg-gagaatcaggca and HAL (Ac153) R: ttaattttcaaacccaaaat-taacagt), a downstream homologous arm HAR(Ac153) (SEQ ID No. 17) was amplified by using primers (HAR (Ac153)-F: tgtgatatgaaatgtatata and HAR(Ac153) R: atgcaagaattgtatgttgct), and a homologous recombinant vector containing the ITR core expression element (ITR GOI) and targeting an essential gene Ac153 gene in the baculoviral genome was constructed. Then, referring to Step 1.1.4 in Example 1, the ITR-GOI was inserted at 1368 bp at the C-terminal of the essential gene Ac153 gene in the recombinant baculoviral genome obtained from 2.2.1, and positive monoclonal strains were selected and named DH10Bac A CCCap Rep(GP64) ITR GOI (Ac153). The bacmid was extracted to obtain a recombinant bacmid numbered Ac 141 174, which contained the recombinant baculoviral genome with the capsid protein gene expression cassette (Cap), Rep gene expression cassette (Rep) and ITR core element for producing the rAAV.

The passage stability test for BEV was carried out according to the method in Example 2. P1-P3 were only tested, with the test data shown below.

TABLE 2

| Category | Passage | Cell packaging efficiency (VG/cell) | Supernatant titer of rAAVs (VG/mL) | Tn7/ GP64 | REP/ GP64 |
|---|---|---|---|---|---|
| Ac-141-174 | P1 | 3.74E+04 | 2.73E+10 | NA | NA |
| | P2 | 1.54E+04 | 1.12E+10 | NA | NA |
| | P3 | 1.42E+04 | 2.67E+09 | 1.42% | 81.24% |

Similar to Example 6, the cell packaging efficiency of Ac-141-174 viruses was low, and the percentage of Tn7/GP64 was very low, indicating that the ITR-GOI expression cassette was inappropriately placed next to the essential gene Ac153. Based on analysis, the reason may lie in that placing the ITR-GOI at the C-terminal of the essential gene Ac153 (equivalent to placing it in front of a start codon at the N-terminal of the Ac154 gene) may affect the expression of the Ac154 gene, which further affects the proliferation of the baculovirus. Therefore, placing the ITR-GOI expression cassette at the C-terminal of the essential gene Ac154 may not be the optimal choice.

For those skilled in the art, it is easy to understand that described above are merely preferred embodiments of the present invention, and are not intended to limit the present invention. Within the spirit and principles of the present invention, any modifications, equivalent substitutions, improvements, and the like should be included within the protection scope of the present invention.

What is claimed is:

1. A preparation method of a recombinant adeno-associated virus, comprising:

Step (1) constructing a recombinant bacmid containing a recombinant baculoviral genome for the recombinant adeno-associated virus production, the recombinant baculoviral genome contains essential functional elements for the recombinant adeno-associated virus production, and the essential functional elements include a Cap gene, a Rep gene, and a core expression element ITR-GOI which carries an exogenous gene of interest; and Step (2) transfecting the recombinant bacmid obtained from Step (1) into a host cell line for culture, wherein at least one of the essential functional elements is inserted into a N-terminal or a C-terminal of an essential genetic locus of the recombinant baculoviral genome, the essential genetic locus of the recombinant baculoviral genome is selected from a group consisting of Ac6, Ac9, Ac10, Ac17, Ac66, Ac109, Ac139, Ac135, Ac98, Ac147, and Ac128, and at least one of the essential functional elements is located within a range of 3 kb of an essential gene expression cassette of the recombinant baculoviral genome, wherein Step (1) includes following steps:

Step (1-1) constructing a homologous recombination vector containing one or two of the essential functional elements; and inserting AAV essential functional elements in the homologous recombination vector into the N-terminal or the C-terminal of one or two of the essential genetic loci of the recombinant baculoviral genome by Red homologous recombination;

Step (1-2) constructing a shuttle plasmid containing remaining essential functional elements; and Step (1-3) integrating a Cap gene expression cassette, a Rep gene expression cassette, and the core expression element ITR-GOI which carries the exogenous gene of interest into a baculoviral genome by Tn7 recombination mediated by the shuttle plasmid, to obtain the recombinant bacmid containing the recombinant baculoviral genome of all of the essential functional elements for the recombinant adeno-associated virus production.

2. The preparation method according to claim 1, wherein at least one of the essential functional elements is located within a range of 1.5 kb of the essential gene expression cassette of the recombinant baculoviral genome.

3. The preparation method according to claim 1, wherein the remaining essential functional elements are inserted into a non-essential genetic locus of the recombinant baculoviral genome.

* * * * *